US007563608B2

(12) United States Patent
Ishikawa et al.

(10) Patent No.: US 7,563,608 B2
(45) Date of Patent: Jul. 21, 2009

(54) METHOD FOR MANUFACTURING A SINTERED COMPACT FOR USE AS A CELL CULTURE BASE

(75) Inventors: Tsuyoshi Ishikawa, Tokyo (JP); Kazuyoshi Yamaguchi, Tochigi (JP); Asako Matsushima, Saitama (JP)

(73) Assignee: Hoya Corporation, Tokyo (JP)

( * ) Notice: Subject to any disclaimer, the term of this patent is extended or adjusted under 35 U.S.C. 154(b) by 635 days.

(21) Appl. No.: 10/638,338

(22) Filed: Aug. 12, 2003

(65) Prior Publication Data

US 2004/0099998 A1   May 27, 2004

(30) Foreign Application Priority Data

| Aug. 12, 2002 | (JP) | 2002-235210 |
| Nov. 22, 2002 | (JP) | 2002-339822 |
| Jul. 4, 2003 | (JP) | 2003-271182 |

(51) Int. Cl.
C12N 11/14 (2006.01)
C12N 5/00 (2006.01)
C04B 35/00 (2006.01)

(52) U.S. Cl. .......................... 435/176; 435/395; 501/1
(58) Field of Classification Search ........................ None
See application file for complete search history.

(56) References Cited

U.S. PATENT DOCUMENTS

| 4,113,500 A | 9/1978 | Ebihara et al. ............. 106/39.5 |
| 4,149,894 A | 4/1979 | Ebihara et al. ............. 106/39.5 |
| 4,230,455 A | 10/1980 | Hidaka et al. ............... 433/202 |
| 4,767,583 A | 8/1988 | Van Der Meer et al. ........ 264/63 |
| 4,919,751 A | 4/1990 | Sumita et al. ................ 154/646 |
| 4,957,674 A | 9/1990 | Ichitsuka et al. .............. 264/65 |
| 5,018,847 A | 5/1991 | Ojima et al. ................ 350/534 |
| 5,089,195 A | 2/1992 | Ichitsuka et al. .............. 264/65 |
| 5,718,855 A | 2/1998 | Akahori et al. ............. 264/122 |
| 6,013,591 A | 1/2000 | Ying et al. ...................... 501/1 |
| 6,323,146 B1 | 11/2001 | Pugh et al. |
| 6,585,992 B2 | 7/2003 | Pugh et al. |
| 6,815,384 B2 | 11/2004 | Ishikawa ...................... 501/1 |
| 6,846,493 B2 | 1/2005 | Pugh et al. |
| 2002/0042657 A1 | 4/2002 | Pugh et al. |
| 2003/0003160 A1 | 1/2003 | Pugh et al. |
| 2003/0176268 A1 | 9/2003 | Ishikawa ...................... 501/1 |
| 2007/0184035 A1 | 8/2007 | Pugh et al. |

FOREIGN PATENT DOCUMENTS

| DE | 102 52 798 | 5/2003 |
| EP | 0291016 | 11/1988 |
| GB | 2142919 | 1/1985 |
| GB | 2 384 208 | 7/2003 |
| GB | 2384208 | 7/2003 |
| JP | 63-129057 | 6/1963 |
| JP | 62-257380 | 11/1987 |
| JP | 2-150271 | 6/1990 |
| JP | 3-290183 | 12/1991 |
| JP | 6-007148 | 1/1994 |
| JP | 6-144918 | 5/1994 |
| JP | 2657403 | 6/1997 |
| JP | 2001-163662 | 6/2001 |
| JP | 2001-259017 | 9/2001 |
| JP | 2001-264247 | 9/2001 |
| JP | 2003-047461 | 2/2003 |
| JP | 2003-146740 | 5/2003 |
| WO | 97/09286 | 3/1997 |
| WO | 00/66036 | 11/2000 |
| WO | 03/012079 | 2/2003 |

OTHER PUBLICATIONS

English Language Abstract of JP 2003-047461.
English Language Abstract of JP 2001-259017.
English Language Abstract of JP 6-144918.
J.A. Delgado et al., Zirconia-Toughened Hydroxyapatite Ceramic Obtained by Wet Sintering, Journal of Materials Science, Materials in Medicine, vol. 10, No. 12, pp. 715-719 (1999), Chapman and Hall, London, GB.
Anna Slosarczyk et al., "Ceramic Materials on the Basis of Hydroxyapatite and Tricalcium Phosphate", Ceramics International, vol. 25, No. 6, pp. 561-565 (1999), Elsevier Applied Science Publ., Barking, Essex, GB.
English Language Abstract of WPI 1990-221161.
English Language Abstract of WPI 1994-053244.
English Language Abstract of WPI 1987-352966.
English Language Abstract of WPI 1992-051435.
English language Abstract of JP 2-150271, Jun. 8, 1990.
English language Abstract of JP 60-07148, Jan. 18, 1994.

(Continued)

*Primary Examiner*—David M Naff
(74) *Attorney, Agent, or Firm*—Greenblum & Bernstein, P.L.C.

(57) ABSTRACT

A method for manufacturing a sintered compact having high density, and a sintered compact manufactured by the manufacturing method are provided. The manufacturing method comprises the steps of preparing hydroxyapatite powder, molding a green compact, shaping the green compact, and sintering the green compact. Further, a method for manufacturing a sintered compact having high light permeability, and a sintered compact manufactured by the manufacturing method are provided. The manufacturing method comprises the steps of preparing hydroxyapatite powder, molding a green compact, shaping the green compact, primary sintering, and secondary sintering. Furthermore, a cell culture base formed from the sintered compact described above is provided, by which affinity of various cells with bone can be properly determined. Moreover, a cell culture base by which affinity of various cells with bone can be properly determined is provided. The cell culture base is mainly composed of a calcium phosphate based compound, and is highly compacted.

8 Claims, 8 Drawing Sheets

OTHER PUBLICATIONS

English language Abstract of JP 62-257380, Nov. 9, 1987.
English language Abstract of JP 3-290183, Dec. 19, 1991.
English Language Abstract of JP 2001-264247.
English Language Abstract of JP 2003-047461.
English Language Abstract of JP 2001-259017.
English Language Abstract of JP 6-144918(1994).

METHOD FOR MANUFACTURING A SINTERED COMPACT FOR USE AS A CELL CULTURE BASE

BACKGROUND OF THE INVENTION

1. Field of the Invention

The present invention relates to a method for manufacturing a sintered compact, a sintered compact manufactured by the method and a cell culture base formed from the sintered compact.

2. Description of the Prior Art

Hydroxyapatite, which is a kind of calcium phosphate based ceramics, is the main component of bone and teeth, and therefore it has excellent biocompatibility. Such hydroxyapatite is used as biomaterial for artificial bone, dental implants, medical or dental cement, and the like. Further, since hydroxyapatite has high affinity with cells, proteins or the like, it is also used as a material for a carrier for cell culture, or a material for use in separation of proteins, or the like. For example, Japanese Patent Laid-open No. 2003-047461 discloses an apatite sheet which is to be used as a carrier for cell culture.

In a case where hydroxyapatite is used as biomaterial for artificial bone or dental implants or the like, sintered compacts of hydroxyapatite are practically used. In this case, the sintered compact is required to have sufficiently high mechanical strength. In order for the sintered compact to meet such requirement, it is necessary for the sintered compact to have high relative density. That is, there is a need to manufacture a high-density sintered compact.

Further, since the occurrence of cracking or the like inside the sintered compact leads to lowering of mechanical strength, inspection of inside of the sintered compact (inspection for determining whether or not cracking or the like exists) is made after manufacturing. For this reason, it is preferred that the sintered compact has transparency.

The transparency of the sintered compact tends to increase with increase in density. From such a viewpoint, it is important to manufacture a high-density sintered compact.

Conventionally, such a sintered compact has been manufactured by molding hydroxyapatite powder into a desired shape to obtain a green compact and then sintering the green compact.

However, it is difficult to obtain a sintered compact having satisfactorily high relative density (that is, high-density sintered compact) by such a conventional manufacturing method.

Further, in the apatite sheet disclosed in Japanese Patent Laid-open No. 2003-047461 mentioned above, the condition of cells adhering to the apatite sheet is observed using a SEM. In the case where cells are observed with a SEM or the like, the cells will, of course, die. On the other hand, in the case where cells are observed with an optical microscope, it is possible to observe living cells, but it is difficult to observe an interface between the cells and the apatite sheet. This is because the apatite sheet has no light permeability so that it is difficult to optically observe the cells.

For this reason, there are demands for apatite sheets having high light permeability.

Furthermore, in recent years, in various kinds of cell culture, there is a case where an instrument having surfaces to be contacted with cells which are coated with a calcium phosphate based material is used. By using such an instrument, cells can be cultured under conditions similar to those in a living body (see Japanese Patent No. 2657403, for example).

Further, since the calcium phosphate based material is a main component of bone, it is also possible to make an evaluation of affinity of various kinds of cells with bone by using such an instrument.

Such an instrument is made by coating a metallic, plastic, or glass substrate with a calcium phosphate based material. However, it is hard to say that the substrate is completely coated with a calcium phosphate based material, so that there is a possibility that a part of the substrate is exposed. Therefore, in a case where such an instrument of which substrate is partially exposed is used, there is a possibility that affinity of cells with glass or the like is evaluated instead of affinity of cells with a calcium phosphate based material (that is, bone).

Further, it is desired that an instrument itself with cultured cells can be transplanted into a living body after the completion of cell culture. However, a problem exists in that since such an instrument is mainly made from glass or the like, the instrument itself can not be transplanted into a living body as it is.

SUMMARY OF THE INVENTION

Therefore, it is an object of the present invention to provide a method for manufacturing a sintered compact by which a high-density sintered compact can be manufactured without the use of large-scale equipment, and a sintered compact manufactured by the manufacturing method.

It is another object of the present invention to provide a method for manufacturing a sintered compact having high light permeability, in particular having light permeability capable of transmitting lights of various wavelengths, and a sintered compact manufactured by the manufacturing method.

It is other object of the present invention to utilize the sintered compact as a cell culture base by which affinity of various cells with bone can be properly determined.

It is yet other object of the present invention to provide a cell culture base by which affinity of various cells with bone can be properly determined.

To achieve the objects described above, the present invention is directed to a method for manufacturing a sintered compact, comprising the steps of:

molding a green compact by compacting hydroxyapatite powder with applying a pressure of 1 ton/cm$^2$ or higher thereto; and sintering the green compact in an oxygen-containing atmosphere, in which the partial pressure of oxygen is higher than that in an atmospheric air, at a temperature in the range of 925 to 1,300° C. to obtain a sintered compact. This makes it possible to obtain a high-density sintered compact.

In this invention, it is preferred that the pressure is isotropically applied to the hydroxyapatite powder. In this case, the isotropic pressure is preferably applied by hydrostatic pressing. This makes it possible to obtain a higher-density sintered compact. Further, the hydrostatic pressing is preferably carried out at a temperature in the range of 5 to 50° C. By using such a method, a green compact can be produced with simple equipment. Therefore, such a method is practically useful as a technique for use in manufacturing industrial products.

Further, in this invention, it is also preferred that the partial pressure of oxygen in the oxygen-containing atmosphere is 380 mmHg or higher. This makes it possible to obtain a higher-density sintered compact.

Furthermore, in this invention, it is also preferred that the hydroxyapatite powder is prepared from a slurry which is obtained by reacting a calcium source with a phosphoric acid source using a wet synthesis method, in which at least one of the calcium source and the phosphoric acid source is used in a liquid form. This makes it possible to easily and efficiently synthesize hydroxyapatite without the requirement for expensive manufacturing equipment. In this case, the calcium source preferably contains calcium hydroxide or calcium oxide as a main ingredient, and the phosphoric acid source preferably contains phosphoric acid as a main ingredient. This makes it possible to more efficiently synthesize hydroxyapatite at a low cost. Further, the slurry preferably contains as a secondary reaction product tricalcium phosphate of 0.1 wt % or less. This makes it possible to obtain a higher-density sintered compact. Furthermore, the slurry preferably satisfies the following condition A.

The condition A: A part of the slurry is sampled and then subjected to compression molding at a molding pressure of 2 ton/cm$^2$ to form a sample green compact having a detection surface. The sample green compact is then sintered in an atmospheric air at 1,200° C. for 2 hours to obtain a sample sintered compact, and then substances which exist on the detection surface (having a surface roughness Ra of 10 μm) of the sample sintered compact are analyzed by x-ray diffraction. At this time, the intensity of a peak derived from hydroxyapatite is the largest among obtained peaks and a peak derived from tricalcium phosphate as a secondary reaction product is not observed. By using such a slurry, it is possible to obtain an especially high-density sintered compact. Moreover, the content of the calcium hydroxide or calcium oxide contained in the slurry is preferably in the range of 0 to 3 wt %. This makes it possible to obtain a higher-density sintered compact. Moreover, the slurry preferably satisfies the following condition B.

The condition B: A part of the slurry is sampled and then subjected to compression molding at a molding pressure of 2 ton/cm$^2$ to form a sample green compact having a detection surface. The sample green compact is then sintered in an atmospheric air at 1,200° C. for 2 hours to obtain a sample sintered compact, and then substances which exist on the detection surface (having a surface roughness Ra of 10 μm) of the sample sintered compact are analyzed by X-ray diffraction. At this time, when the intensity of a peak derived from hydroxyapatite is defined as X and the intensity of a peak derived from calcium oxide is defined as Y, X and Y satisfy the relation Y/X<1/10. By using such a slurry, it is possible to obtain an especially high-density sintered compact. Moreover, in this invention, it is also preferred that when the sintered compact is formed into a sheet form having a thickness of 15 mm and then thus obtained sheet form sintered compact is irradiated with light having a luminance of 230,000 cd/m$^2$ and having color expressed by chromaticity coordinates (0.543, 0.4) on the CIE chromaticity diagram, the luminance of transmitted light through the sintered compact is 150 cd/m$^2$ or higher. Since such a sintered compact (test piece) having the characteristic mentioned above is considered to have relatively high transparency, the sintered compact manufactured under the same conditions as those for the test piece is believed to have relatively high transparency. When the sintered compact has such high transparency, it is possible to easily detect the presence or absence of sintering flaws such as cracking or the presence or absence of contamination in the inside of the sintering compact after sintering.

Another aspect of the present invention is directed to a method for manufacturing a sintered compact, comprising the steps of:

molding a green compact by compacting apatite powder with applying a pressure of 1 ton/cm$^2$ or higher thereto;

sintering the green compact by subjecting the green compact to primary sintering in an oxygen-containing atmosphere in a sintering furnace in which a volume ratio of oxygen in a gas existing in the sintering furnace is 50 vol % or more, thereby obtaining a sintered compact; and subjecting the sintered compact to secondary sintering in an atmosphere with low level of activity. This makes it possible to obtain a sintered compact which has high density and allows lights of various wavelengths to pass therethrough.

In this invention, it is preferred that the pressure is isotropically applied to the apatite powder in the step of molding the green compact. In this case, the pressure is preferably isotropically applied to the apatite powder in the step of molding the green compact. This makes it possible to obtain a higher-density sintered compact. Further, the hydrostatic pressing is preferably carried out at a temperature in the range of 5 to 50° C. By using such a method, a green compact can be produced with simple equipment. Therefore, such a method is practically useful as a technique for use in manufacturing industrial products.

Further, in this invention, it is also preferred that the partial pressure of oxygen in the oxygen-containing atmosphere in the primary sintering step is 380 mmHg or higher. This makes it possible to obtain a higher-density sintered compact.

Furthermore, in this invention, it is also preferred that the pressure of the oxygen-containing atmosphere in the primary sintering step is 900 mmHg or lower. This makes it possible to obtain a sintered compact having higher light permeability.

Moreover, in this invention, it is also preferred that a temperature during sintering of the green compact in the primary sintering step is in the range of 850 to 1,350° C. This makes it possible to more reliably sinter the green compact.

Moreover, in this invention, it is also preferred that the atmosphere with low level of activity in the secondary sintering step is a nitrogen gas atmosphere or an inert gas atmosphere. Such gases are preferred in that they have extremely low reactivity to apatite.

Moreover, in this invention, it is also preferred that a temperature during sintering of the sintered compact in the secondary sintering step is in the range of 1,000 to 1,350° C. By setting the temperature during the secondary sintering step to such a range, it is possible for the obtained sintered compact to allow light having wavelengths shorter than those of visible light to pass therethrough reliably.

Moreover, in this invention, it is also preferred that the mean particle size of the apatite powder is 40 μm or less. This makes it possible to obtain a higher-density sintered compact.

Moreover, in this invention, it is also preferred that the primary and secondary sintering steps are carried out in the same sintering furnace by changing an atmosphere in the sintering furnace from the oxygen-containing atmosphere in the primary sintering step to the atmosphere with low level of activity in the secondary sintering step. By doing so, it is possible to manufacture a sintered compact in a shorter period of time.

Moreover, in this invention, it is also preferred that the apatite powder is hydroxyapatite powder. By using hydroxyapatite as apatite, the obtained sintered compact can be more suitably used as a biomaterial or a carrier for cell culture. In this case, the hydroxyapatite powder is preferably prepared from a slurry which is obtained by reacting a calcium source with a phosphoric acid source using a wet synthesis method, in which at least one of the calcium source and the phosphoric acid source is used in a liquid form. This makes it possible to easily and efficiently synthesize hydroxyapatite without the requirement for expensive equipment. Further, the calcium source preferably contains calcium hydroxide or calcium oxide as a main ingredient, and the phosphoric acid source preferably contains phosphoric acid as a main ingredient.

This makes it possible to more efficiently synthesize hydroxyapatite at a low cost. Furthermore, the slurry preferably contains as a secondary reaction product tricalcium phosphate of 0.1 wt % or less. This makes it possible to obtain a higher-density sintered compact. Moreover, the slurry preferably satisfies the following condition A.

The condition A: A part of the slurry is sampled and then subjected to compression molding at a molding pressure of 2 ton/cm² to form a sample green compact having a detection surface. The sample green compact is then sintered in an atmospheric air at 1,200° C. for 2 hours to obtain a sample sintered compact, and then substances which exist on the detection surface (having a surface roughness Ra of 10 µm) of the sample sintered compact are analyzed by x-ray diffraction. At this time, the intensity of a peak derived from hydroxyapatite is the largest among obtained peaks and a peak derived from tricalcium phosphate as a secondary reaction product is not observed. By using such a slurry, it is possible to obtain an especially high-density sintered compact. Moreover, the content of the calcium hydroxide or calcium oxide contained in the slurry is preferably in the range of 0 to 3 wt %. This makes it possible to obtain a higher-density sintered compact. Moreover, the slurry preferably satisfies the following condition B.

The condition B: A part of the slurry is sampled and then dried at 200° C. to obtain a sample. The sample is then sintered in an atmospheric air at 1,200° C. for 20 minutes to obtain a sintered sample, and then substances which exist in the sintered sample are analyzed by powder X-ray diffraction. At this time, when the intensity of a peak derived from hydroxyapatite is defined as X and the intensity of a peak derived from calcium oxide is defined as Y, X and Y satisfy the relation Y/X<1/10. By using such a slurry, it is possible to obtain an especially high-density sintered compact.

Moreover, in this invention, it is also preferred that the relative density of the sintered compact after the primary sintering is 99% or higher. This makes it possible for the sintered compact to allow light having wavelengths shorter than those of visible light to pass therethrough more reliably.

Moreover, in this invention, it is also preferred that when the sintered compact is formed into a sheet form having a thickness of 0.5 mm and then thus obtained sheet form sintered compact is irradiated with light having wavelength of 300 nm, the transmittance of the light passing through the sintered compact is 10% or higher. Since such a sintered compact (test piece) allows light having wavelengths shorter than those of visible light to pass therethrough efficiently, a sintered compact manufactured under the same conditions as those for the test piece is also believed to allow light having wavelengths shorter than those of visible light to pass therethrough efficiently.

Yet another aspect of the present invention is directed to a sintered compact which is manufactured according to the method for manufacturing a sintered compact described above.

In this invention, it is preferred that the sintered compact is formed into a cell culture base. In this case, the cell culture base preferably has a flat plate portion having first and second surfaces, in which cells are adapted to adhere to one of the first and second surfaces for growing the cells. Further, it is preferred that the flat plate portion of the cell culture base is mainly composed of hydroxyapatite or apatite having a relatively high density. This makes it possible to determine the affinity of various cells with bone. Furthermore, the flat plate portion of the cell culture base preferably has a porosity of 1% or less. This makes it possible to further increase the transparency of the flat plate portion. Moreover, the flat plate portion of the cell culture base preferably has an average thickness of 0.1 to 3 mm. This makes it possible for the flat plate portion to have sufficiently high transparency without decrease in strength of the flat plate portion. Moreover, at least the one of the first and second surfaces of the flat plate portion of the cell culture base is preferably formed into a rough surface. This allows cells to adhere to the one surface of the flat plate portion more easily and reliably. In this case, the rough surface is preferably formed by grinding the one surface with a grinding material containing particles having a mean particle size in the range of 5 to 30 µm, or the rough surface preferably has substantially the same surface roughness as that obtained by such grinding. This further increases the rate of adhesion of cells to the one surface of the flat plate portion and makes it possible to observe the condition of cells without difficulty.

Moreover, in this invention, it is also preferred that the one surface of the flat plate portion of the cell culture base is formed with a concave part. This further facilitates quick adhesion of cells to the flat plate portion so that more efficient cell culture becomes possible. In this case, the concave part preferably includes at least one groove. This makes it possible for cells to grow along edges of the groove, and therefore, it is possible to easily observe the cells. Further, it is preferred that the horizontal cross-sectional area of the concave part is substantially constant in the depth direction thereof or decreased toward another surface of the flat plate portion. This makes it easy for cells to adhere to the edges of the groove. Furthermore, the percentage of the depth of the concave part to the thickness of the flat plate portion is preferably in the range of 0.005 to 20%. This makes it possible to sufficiently increase the surface area of the one surface of the flat plate portion, while the flat plate portion possesses sufficient strength. Moreover, the percentage of an area occupied by the concave part to the whole surface area of the flat plate portion in a plan view is preferably in the range of 1 to 60%. This makes it possible to sufficiently increase the surface area of the one surface of the flat plate portion.

Moreover, in this invention, it is also preferred that another surface of the flat plate portion is formed into a smooth surface. This prevents the scattering of irradiated light at the another surface of the flat plate portion so that it is possible to observe the condition of cells more properly. In this case, the smooth surface is preferably obtained by polishing the surface with a polishing material containing particles having a mean particle size of 1 µm or less, or the smooth surface has substantially the same surface roughness as that obtained by such polishing. This prevents the scattering of light at the another surface of the flat plate portion more reliably.

Moreover, in this invention, it is also preferred that the condition of the cells is adapted to be observed in a state that light is being allowed to pass through the flat plate portion. This makes it possible to observe the condition of the cells relatively easily without the requirement for large-scale equipment. In this case, the condition of the cells is preferably observed in a state that the light is being allowed to pass through the flat plate portion from the side of the one surface of the flat plate portion. By doing so, it is possible to more properly observe the condition of the cells adhering to the one surface of the flat plate portion.

Moreover, in this invention, it is also preferred that the entire of the cell culture base constitutes the flat plate portion. In this case, the cell culture base is preferably formed into a substantially disc-like shape. Further, the diameter of the cell culture base is preferably in the range of 0.5 to 200 mm.

Still another aspect of the present invention is directed to a cell culture base, comprising:

a flat plate portion having first and second surfaces in which cells are adapted to adhere to one of the first and second surfaces for growing the cells, the flat plate portion of the cell culture base being mainly composed of a calcium phosphate based compound having a relatively high density. This makes it possible to determine the affinity of various cells with bone.

In this invention, it is preferred that the flat plate portion has a porosity of 1% or less. This makes it possible to further increase the transparency of the flat plate portion. In this case, the flat plate portion preferably has an average thickness of 0.1 to 3 mm. This makes it possible for the flat plate portion to have sufficiently high transparency without decrease in strength of the flat plate portion.

Further, in this invention, it is also preferred that at least the one of the first and second surfaces of the flat plate portion is formed into a rough surface. This allows cells to adhere to the one surface of the flat plate portion more easily and reliably. In this case, the rough surface is preferably formed by grinding the one surface with a grinding material containing particles having a mean particle size in the range of 5 to 30 µm, or the rough surface preferably has substantially the same surface roughness as that obtained by such grinding. This further increases the rate of adhesion of cells to the one surface of the flat plate portion and makes it possible to observe the condition of cells without difficulty.

Furthermore, in this invention, it is also preferred that the one surface of the flat plate portion is formed with a concave part. This further facilitates quick adhesion of cells to the flat plate portion so that more efficient cell culture becomes possible. In this case, the concave part preferably includes at least one groove. This makes it possible for cells to grow along edges of the groove, and therefore, it is possible to easily observe the cells. Further, it is preferred that the horizontal cross-sectional area of the concave part is substantially constant in the depth direction thereof or decreased toward another surface of the flat plate portion. This makes it easy for cells to adhere to the edges of the groove. Furthermore, the percentage of the depth of the concave part to the thickness of the flat plate portion is preferably in the range of 0.005 to 20%. This makes it possible to sufficiently increase the surface area of the one surface of the flat plate portion, while the flat plate portion possesses sufficient strength. Moreover, the percentage of an area occupied by the concave part to the whole surface area of the flat plate portion in a plan view is preferably in the range of 1 to 60%. This makes it possible to sufficiently increase the surface area of the one surface of the flat plate portion.

Moreover, in this invention, it is also preferred that another surface of the flat plate portion is formed into a smooth surface. This prevents the scattering of irradiated light at the another surface of the flat plate portion so that it is possible to observe the condition of cells more properly. In this case, the smooth surface is preferably obtained by polishing the surface with a polishing material containing particles having a mean particle size of 1 µm or less, or the smooth surface has substantially the same surface roughness as that obtained by such polishing. This prevents the scattering of light at the another surface of the flat plate portion more reliably.

Moreover, in this invention, it is also preferred that the condition of the cells is adapted to be observed in a state that light is being allowed to pass through the flat plate portion. This makes it possible to observe the condition of the cells relatively easily without the requirement for large-scale equipment. In this case, the condition of the cells is preferably observed in a state that the light is being allowed to pass through the flat plate portion from the side of the one surface of the flat plate portion. By doing so, it is possible to more properly observe the condition of the cells adhering to the one surface of the flat plate portion.

Moreover, in this invention, it is also preferred that the entire of the cell culture base constitutes the flat plate portion. In this case, the cell culture base is preferably formed into a substantially disc-like shape. Further, the diameter of the cell culture base is preferably in the range of 0.5 to 200 mm.

Moreover, in this invention, it is also preferred that the calcium phosphate based compound is tricalcium phosphate. Since tricalcium phosphate is close to the ingredient of bone, it is possible to more properly determine the affinity of various cells with bone.

Moreover, in this invention, it is also preferred that the calcium phosphate based compound is hydroxyapatite. Since hydroxyapatite is the main ingredient of bone, it is possible to more properly determine the affinity of various cells with bone.

DETAILED DESCRIPTION OF THE INVENTION

Hereinbelow, a detailed description will be made with regard to preferred embodiments of a method for manufacturing a sintered compact and a sintered compact manufactured by the method according to the present invention as well as preferred embodiments of a cell culture base formed from the sintered compact.

Figure 1:
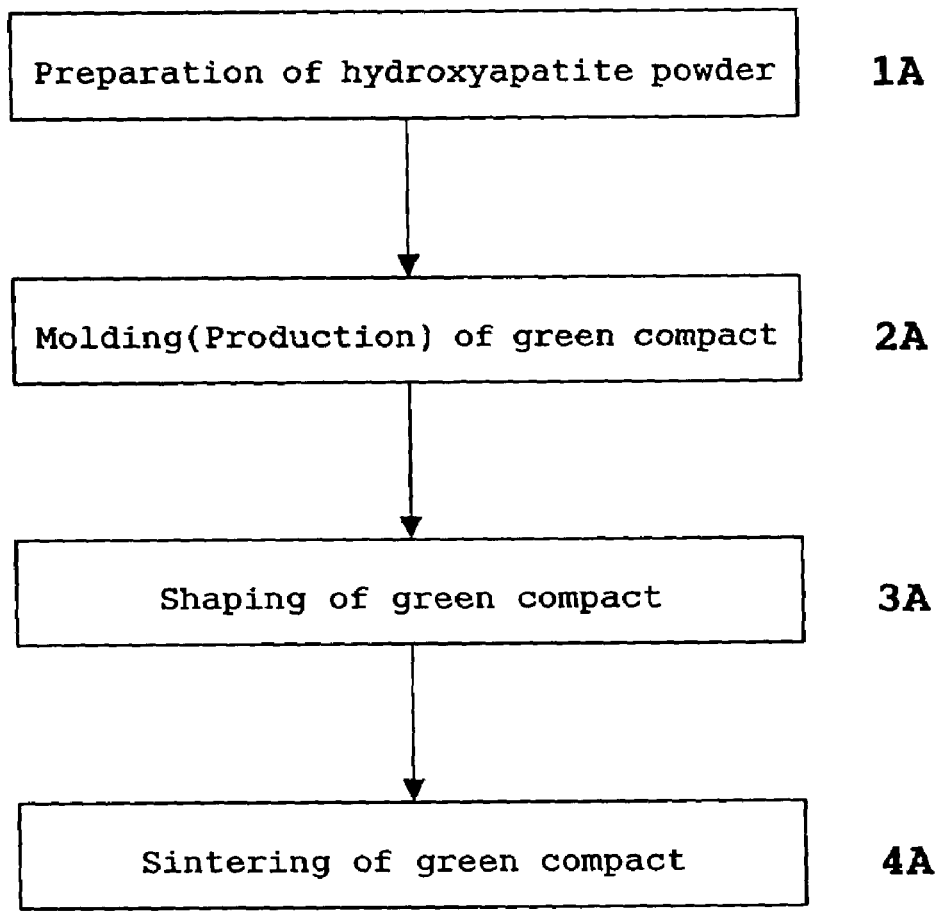
FIG. 1 is a step diagram which shows a first embodiment of a method for manufacturing a sintered compact according to the present invention.

FIG. 1 is a step diagram which shows a first embodiment of the method for manufacturing a sintered compact according to the present invention. The sintered compact manufacturing method shown in FIG. 1 comprises a step of preparing hydroxyapatite powder (step 1A), a step of molding (production) of a green compact (step 2A), a step of shaping the green compact into a desired form or size (step 3A), and a step of sintering the green compact (step 4A). Each of the steps will now be described in this order.

<1A> Preparation of Hydroxyapatite Powder

First, a calcium source is reacted with a phosphoric acid source to synthesize hydroxyapatite (HAp). It is to be noted here that in this embodiment the term "hydroxyapatite" means hydroxyapatite having a mole ratio of Ca to P (Ca/P) of 1.60 to 1.70.

Such hydroxyapatite can be synthesized by any method such as a wet synthesis method, a dry synthesis method or a hydrothermal synthesis method or the like. Among them, a wet synthesis method in which at least one of the calcium source and the phosphoric acid source is used in a liquid form is preferable. According to such a wet synthesis method, it is possible to easily and efficiently synthesize hydroxyapatite without the requirement for expensive manufacturing equipment.

In a case where the wet synthesis method is employed, calcium hydroxide, calcium oxide, calcium nitrate or the like can be used as a calcium source, for example. As for a phosphoric acid source, phosphoric acid, ammonium phosphate or the like can be used. Among them, a calcium source containing calcium hydroxide or calcium oxide as a main ingredient, and a phosphoric acid source containing phosphoric acid as a main ingredient are particularly preferable. By using such calcium source and phosphoric acid source, it is possible to more efficiently synthesize hydroxyapatite at a low cost.

Hereinafter, a description will now be made with regard to a case where a calcium source containing calcium hydroxide or calcium oxide as a main ingredient and a phosphoric acid source containing phosphoric acid as a main ingredient are used.

In this case, hydroxyapatite (HAp) is synthesized by, for example, dropping a phosphoric acid solution ($H_3PO_4$) into a suspension of calcium hydroxide ($Ca(OH)_2$) or calcium oxide (CaO) within a vessel and then mixing them.

The reaction can be represented by the following equation (I) or (II)

$$10Ca(OH)_2 + 6H_3PO_4 \rightarrow 2Ca_5(PO_4)_3(OH) + 18H_2O \quad (I)$$

$$10CaO + 10H_2O + 6H_3PO_4 \rightarrow 2Ca_5(PO_4)_3(OH) + 18H_2O \quad (II)$$

In this case, if the reaction does not sufficiently proceed, an unreacted substance ($Ca(OH)_2$ or CaO) will exist as an impurity in a resultant mixture in a slurry state (hereinafter, simply referred to as a "slurry").

Further, when the reaction still goes on, another reaction represented by the following equation (III) occurs, and as a result tricalcium phosphate (TCP) is generated as a secondary reaction product.

$$3Ca_5(PO_4)_3(OH) + H_3PO_4 \rightarrow 5Ca_3(PO_4)_2 + 3H_2O \quad (III)$$

If this reaction occurs, tricalcium phosphate which is a secondary reaction product will exist in the resultant slurry as an impurity.

In this fist embodiment of the sintered compact manufacturing method of the present invention, hydroxyapatite powder is prepared from the slurry containing hydroxyapatite synthesized in this manner. In connection with this, the present inventors have found that by using hydroxyapatite powder prepared from a slurry hardly containing the impurities mentioned above, it is possible for an obtained sintered compact to have high relative density, that is, it is possible to obtain a high-density sintered compact.

A description will now be made with regard to a preferred range of contents (concentrations) of each of tricalcium phosphate and unreacted substances ($Ca(OH)_2$, CaO) in the slurry.

(Tricalcium Phosphate)

The content (concentration) of tricalcium phosphate in the slurry is not limited to any specific value, but is preferably equal to or less than 0.1 wt %, and more preferably 0 wt %. When the content of tricalcium phosphate in the slurry lies within such a range, that is, by using the slurry containing less or no tricalcium phosphate, it is possible for a resultant sintered compact to have higher density.

Further, it is most suitable that the slurry satisfies the condition A described below.

The condition A: A part of the slurry is sampled and then subjected to compression molding at a molding pressure of 2 ton/cm$^2$ to form a sample green compact having a detection surface. The sample green compact is sintered in an atmospheric air at 1,200° C. for 2 hours to obtain a sample sintered compact, and then substances which exist on the detection surface (having a surface roughness Ra of 10 μm) of the sample sintered compact are analyzed by x-ray diffraction. At this time, the intensity of a peak derived from hydroxyapatite is the largest among obtained peaks and a peak derived from tricalcium phosphate is not observed.

Such an analytical method is based on the fact that in the sintering process described above, grain growth of hydroxyapatite occurs prior to that of the impurities due to the difference in their sintering rates, and as a result the impurities are excluded from a void between the grains and then deposited on the surface of the sample sintered compact (in particular, on the detection surface). Therefore, by analyzing the detection surface by means of the X-ray diffraction, it is possible to detect the presence or absence of the impurities. According to this analytical method, it is possible to determine whether or not the impurities exist in the slurry with high accuracy.

When the slurry satisfies the condition A, it is confirmed that the slurry does not contain tricalcium phosphate or even if the slurry contains tricalcium phosphate, the amount thereof is extremely small. Therefore, by using such a slurry, it is possible to obtain especially high-density sintered compacts.

(Unreacted Substance)

The content (concentration) of the unreacted substance in the slurry is not limited to any specific value, but is preferably in the range of about 0 to 3 wt %, and more preferably in the range of about 0.025 to 1 wt %. Even if a relatively small amount of the unreacted substance such as calcium oxide exists in the slurry, calcium oxide tends to increase the relative density of a resultant sintered compact (Note that, in a case where the unreacted substance is calcium hydroxide, calcium hydroxide is changed into calcium oxide due to sintering). As a result, an obtained sintered compact can have higher density. If the content of the unreacted substance in the slurry exceeds the above upper limit value, there is a case where it becomes difficult to obtain high-density sintered compacts depending on conditions during sintering of the green compacts (which will be described later).

Further, it is also most suitable that the slurry satisfies the condition B described below.

The condition B: A part of the slurry is sampled and then subjected to compression molding at a molding pressure of 2 ton/cm$^2$ to form a sample green compact having a detection surface. The sample green compact is sintered in an atmospheric air at 1,200° C. for 2 hours to obtain a sample sintered compact, and then substances which exist on the detection surface (having a surface roughness Ra of 10 μm) of the sample sintered compact are analyzed by X-ray diffraction. At this time, when the intensity of a peak derived from hydroxyapatite is defined as X and the intensity of a peak derived from calcium oxide is defined as Y, X and Y satisfy the relation Y/X<1/10 (especially, Y/X<1/100).

As described above, according to such an analytical method, it is also possible to determine whether or not the impurities exist in the slurry with high accuracy. When the slurry satisfies the condition B, it is confirmed that the content of the unreacted substance in the slurry is extremely small. By using such a slurry, it is also possible to obtain especially high-density sintered compacts.

Further, at least one of the contents of the tricalcium phosphate and the unreacted substance in the slurry should lie within the range described above, but it is preferred that both of the contents of the tricalcium phosphate and the unreacted substance lie within the respective ranges described above. This makes it possible to obtain extremely high-density sintered compacts.

Next, hydroxyapatite powder (hereinafter, simply referred to as "powder") is prepared by, for example, spray drying the thus obtained slurry.

The mean particle size of the powder is not limited to any specific value, but is preferably in the range of about 1 to 30 μm, and more preferably in the range of about 8 to 25 μm. By using powder having such a mean particle size, it is possible to obtain higher-density sintered compacts.

It is to be noted here that the obtained powder may be subjected to heat treatment under the condition of 500 to 800° C. for 2 to 6 hours, for example, and then milled using, for example, a jet mill or a turbo mill so that the powder has a mean particle size of about 6 to 20 μm (which is about 50 to 80% of a mean particle size before milling). By using such milled powder, it is possible to obtain more closely compacted green compacts.

<2A> Molding (Production) of Green Compact

Next, the thus obtained powder (or a powder compact which has been molded into a desired form in advance) is compacted by the application of pressure.

As for a method of applying pressure, any method such as isotropic pressing, pressing in only one direction (uniaxial direction) e.g., uniaxial pressing, or the like can be employed. Among them, isotropic pressing, especially hydrostatic pressing is preferable. By using such a method, it is possible for a resultant green compact to have uniform density, and as a result, a higher-density sintered compact can be obtained.

As for hydrostatic pressing, CIP (Cold Isostatic pressing) in which pressure is applied at a temperature of about 5 to 50° C. (preferably, about 10 to 30° C.) is suitably used. Since CIP has such advantages that it can be carried out with simple equipment and that a film (which will be described later) is not required to have heat resistance, CIP is practically useful as a technique for use in manufacturing industrial products. Alternatively, HIP (Hot Isostatic pressing) in which pressure is applied with heating (at 65° C. or higher, for example), or Hot press may be employed.

Specifically, in hydrostatic pressing, the powder enclosed with a liquid-proof film is placed in a hydrostatic pressing unit, and then hydrostatic pressure is applied. In the case of CIP, examples of a material of the film include: resin such as polyvinyl chloride, polyethylene, polypropylene and the like; and rubber such as natural rubber and isoprene rubber. The film can be formed by, for example, dipping or vacuum packing.

A pressure to be applied is 1 ton/cm² or higher, more preferably in the range of about 1 to 3 ton/cm², and even more preferably in the range of about 2 to 3 ton/cm². If the pressure is too low, there is a case where a sufficient effect by pressing (especially, uniformity in density) can not be expected. On the other hand, even if the pressure is increased so as to exceed the above upper limit value, an improved effect can not be obtained. Further, use of such an increased pressure requires large-scale equipment, thus resulting in an increased equipment cost.

The green compact obtained by applying pressure in this manner can have high and uniform density. When such a green compact is sintered as described below, the green compact is uniformly shrunk. Therefore, a finally obtained sintered compact has high dimensional accuracy. Further, such uniform density suppresses the occurrence of sintering flaws such as cracking, chipping and the like in the sintered compact, and therefore such a sintered compact is hard to be damaged (that is, it has excellent mechanical strength). In this connection, it is to be noted that the film covering the surface of the powder is removed by a predetermined method after pressing.

<3A> Shaping of Green Compact

Next, the thus obtained green compact is shaped into a desired form or size, as necessary.

The green compact is shaped by, for example, subjecting it to a predetermined machine working. Examples of the machine working include cutting, grinding, polishing and the like, and they can be carried out singly or in combination of two or more.

Since the hardness of the green compact itself is very low as compared with that of a finally obtained sintered compact, it is possible to easily carry out the machine working or the like onto the green compact. In particular, the green compact has advantages in that machine working can be carried out with low hardness tools and it takes shorter time to complete the machine working.

<4A> Sintering of Green Compact

The thus obtained green compact is sintered (fired) in an oxygen-containing atmosphere in a sintering furnace for example, in which the partial pressure of oxygen is higher than that in an atmospheric air, to thereby obtain a sintered compact.

The present inventors have conducted extensive researches, and as a result found that by sintering the green compact in an oxygen-containing atmosphere in which the partial pressure of oxygen is higher than that in an atmospheric air, it is possible to obtain especially high-density sintered compacts.

A typical example of such an oxygen-containing atmosphere (sintering atmosphere) includes a pure oxygen atmosphere. Alternatively, a mixed gas of oxygen and other gases (in particular, a mixed gas mainly containing oxygen) may be used as the oxygen-containing atmosphere.

Further, in a case where the green compact is sintered under a pressure higher than atmospheric pressure (2 to 10 atoms, for example), an atmospheric air may be used as the oxygen-containing atmosphere, because a resultant partial pressure of oxygen becomes higher than that in an atmospheric air.

It is to be noted here that in a case where the green compact is sintered under atmospheric pressure (1 atom), it is not necessary for a sintering furnace to have high airtightness. Therefore, sintering under atmospheric pressure is preferred in that a sintering furnace can be simplified, thus resulting in a reduced manufacturing cost of sintered compacts.

The partial pressure of oxygen in the oxygen-containing atmosphere (in the case of a pure oxygen atmosphere, the partial pressure of oxygen means a pressure in the sintering furnace) is preferably equal to or higher than 380 mmHg, and is more preferably equal to or higher than 550 mmHg. By setting the partial pressure of oxygen to the above range, it is possible for an obtained sintered compact to have higher relative density.

In this connection, under atmospheric pressure, by increasing the volume (concentration) of oxygen in the oxygen-containing atmosphere (sintering atmosphere), the partial pressure of oxygen in the oxygen-containing atmosphere becomes high.

Further, the present inventors have also found that by sintering the green compact in such an oxygen-containing atmosphere in which the partial pressure of oxygen is high, it is possible to carry out sintering at a relatively low sintering temperature. In addition, they have also found that the green compact can be sintered while the grain growth of hydroxyapatite is being suppressed, and as a result higher-density sintered compacts can be obtained.

Furthermore, sintering of green compacts at a relatively low temperature also has advantages in that sintering time, energy consumed for sintering and the cost of a heating element used in a sintering furnace can be reduced.

A temperature during sintering (sintering temperature) is in the range of 925 to 1,300° C., and is preferably in the range of about 1,000 to 1,250° C. If the sintering temperature is too low, there is a case that the green compact is not efficiently sintered.

A period of time over which the sintering temperature is being held (sintering time) is preferably in the range of about 30 minutes to 8 hours, and is more preferably in the range of about 2 to 4 hours.

Through the steps described above, a sintered compact of the present invention can be obtained.

Since the sintered compact manufactured by the first embodiment of the manufacturing method of the present invention has high density, mechanical strength thereof is extremely high. Therefore, the sintered compact manufactured by this first embodiment can be suitably used as a biomaterial for artificial bone such as a vertebral spacer, an auditory ossicle and the like, dental implants, and the like. Further, the sintered compact manufactured by this embodiment can be also used as a material for a carrier for cell culture or a cell culture base since hydroxyapatite has high affinity with cells, proteins or the like.

Further, it is preferred that a sintered compact manufactured by this first embodiment of the sintered compact manufacturing method of the present invention has the following characteristic.

Specifically, the characteristic is that when a test piece (sintered compact) in a sheet form having a thickness of 15 mm is prepared, and then it is irradiated with light having a luminance of 230,000 $cd/m^2$ and color expressed by chromaticity coordinates (0.543, 0.4) on the CIE chromaticity diagram, transmitted light through the test piece has a luminance of 150 $cd/m^2$ or more (in particular, 200 $cd/m^2$ or more).

Here, the reason why such a test piece is used will be described below. Namely, the shape and size of the sintered compact to be practically used is appropriately set according to its purpose of use, that is, practically used sintered compacts have various shapes and sizes. Therefore, even if the luminances of transmitted lights through the sintered compacts having the various shapes and sizes are measured under the same condition, evaluations can not be made based on the same standard due to their various shapes and sizes. Therefore, a test piece having the above characteristic is prepared according to the above-described sintered compact manufacturing method. By preparing such a test piece, if a sintered compact to be practically used is manufactured under the same conditions as those for the test piece, it is possible to consider that the sintered compact has a characteristic similar to that of the test piece. Further, since the test piece having the characteristic described above is considered to have relatively high transparency, the sintered compact manufactured under the same conditions as those for the test piece is believed to have relatively high transparency.

When the sintered compact has such high transparency, it is possible to easily detect the presence or absence of sintering flaws such as cracking or the presence or absence of contamination in the inside of the sintered compact after sintering.

Although the sintered compact manufacturing method of the first embodiment of the present invention and the sintered compact manufactured by the method have been described in the above, the present invention is not limited thereto.

For example, the sintered compact manufacturing method of the first embodiment may include a preliminary step coming before the step 1A, an intermediate step coming between the steps 1A to 4A, or a post step coming after the step 4A.

EXAMPLE

Next, actual examples of the first embodiment of the sintered compact manufacturing method of the present invention will be described.

<Manufacture of Sintered Compact>

Sintered compacts of Examples 1A to 10A and Comparative Examples 1A to 4A were manufactured as follows.

Example 1A

<1> First, 140 g of calcium hydroxide was dispersed in 6 liters of pure water, and then an aqueous phosphoric acid solution whose concentration of phosphoric acid was 2 wt % was dropped into the pure water in which calcium hydroxide was dispersed. They were sufficiently mixed with stirring to synthesize hydroxyapatite, and as a result a slurry containing hydroxyapatite was obtained.

Next, the obtained slurry was spray dried using a spray dryer to obtain hydroxyapatite powder having a mean particle size of 20 μm.

At that time, a part of the slurry was sampled and then subjected to compression molding at a molding pressure of 2 $ton/cm^2$ to form a sample green compact having a detection surface. The thus obtained sample green compact was sintered in an atmospheric air at 1,200° C. for 2 hours to obtain a sample sintered compact, and then substances existing on the detection surface (having a surface roughness Ra of 10 μm) of the sample sintered compact were analyzed by X-ray diffraction. In this connection, the sample had a diameter of 15 mm and a height of 8 mm.

As a result of analysis, a peak derived from tricalcium phosphate (TCP) was not observed, and the intensity of a peak derived from calcium oxide (CaO) was 1/250 of that derived from hydroxyapatite (HAp).

The thus obtained hydroxyapatite powder was subjected to heat treatment under the condition of 600° C. for 4 hours, and was then milled using a jet mill. In this way, hydroxyapatite powder having a mean particle size of 16 μm was obtained.

<2> Next, the thus obtained hydroxyapatite powder was compressed into a cylindrical shape by the use of a compression molding machine, and thereafter the powder formed into such a cylindrical shape was put into a plastic bag and vacuum-sealed. Then, a hydrostatic pressure of 1 $ton/cm^2$ was applied to the powder in the plastic bag under room temperature (24° C.), to thereby obtain a cylindrical-shaped green compact having a diameter of 21 mm and a height of 52 mm.

<3> Next, cutting (machine working) was carried out onto the green compact by the use of a diamond cutter so that the green compact was formed into a cylindrical shape having a diameter of 20 mm and a height of 50 mm.

<4> Next, the thus obtained green compact was sintered in a sintering furnace to obtain a sintered compact. In this regard, it is to be noted that sintering was carried out in a pure oxygen atmosphere (sintering atmosphere) at 1,050° C. for 2 hours. At this time, a pressure in the sintering furnace was set to 760 mmHg (1 atom).

Example 2A

A sintered compact was manufactured in the same manner as Example 1A except that the hydrostatic pressure was changed to 1.5 ton/cm² in the process <2> described above.

Example 3A

A sintered compact was manufactured in the same manner as Example 1A except that the hydrostatic pressure was changed to 2.0 ton/cm² in the process <2> described above.

Example 4A

A sintered compact was manufactured in the same manner as Example 3A except that the sintering temperature was changed to 925° C. in the process <4> described above.

Example 5A

A sintered compact was manufactured in the same manner as Example 3A except that the sintering temperature was changed to 950° C. in the process <4> described above.

Example 6A

A sintered compact was manufactured in the same manner as Example 3A except that the sintering temperature was changed to 1,000° C. in the process <4> described above.

Example 7A

A sintered compact was manufactured in the same manner as Example 3A except that the sintering temperature was changed to 1,250° C. in the process <4> described above.

Example 8A

A sintered compact was manufactured in the same manner as Example 3A except that the sintering atmosphere was changed to a mixed gas atmosphere of oxygen and argon gas in the process <4> described above. In this connection, the partial pressure of oxygen was set to 190 mmHg.

Example 9A

A sintered compact was manufactured in the same manner as Example 3A except that the sintering atmosphere was changed to a mixed gas atmosphere of oxygen and argon gas in the process <4> described above. In this connection, the partial pressure of oxygen was set to 380 mmHg.

Example 10A

A sintered compact was manufactured in the same manner as Example 3A except that the sintering atmosphere was changed to a mixed gas atmosphere of oxygen and argon gas in the process <4> described above. In this connection, the partial pressure of oxygen was set to 570 mmHg.

Comparative Example 1A

A sintered compact was manufactured in the same manner as Example 1A except that the hydrostatic pressure was changed to 0.5 ton/cm² in the process <2> described above.

Comparative Example 2A

A sintered compact was manufactured in the same manner as Example 1A except that the sintering atmosphere was changed to a pure argon gas atmosphere in the process <4> described above.

Comparative Example 3A

A sintered compact was manufactured in the same manner as Example 3A except that the sintering atmosphere was changed to an atmospheric air at 1 atm in the process <4> described above.

Comparative Example 4A

A sintered compact was manufactured in the same manner as Example 3A except that the sintering temperature was changed to 900° C. in the process <4> described above.

Evaluation

The relative density of each of the sintered compacts manufactured in Examples 1A to 10A and Comparative Examples 1A to 4A was determined based on its volume defined by external dimensions and its weight, in consideration of specific gravity.

Evaluation results and manufacturing conditions of the sintered compacts of Examples 1A to 10A and Comparative Examples 1A to 4A are shown in Table 1.

TABLE 1

| | Production of green compact | | Sintering of green compact | | | Evaluation results |
|---|---|---|---|---|---|---|
| | Method of pressing | Pressure (ton/cm²) | Sintering atmosphere | Pressure in sintering furnace (mmHg) | Temp. × Time (° C.) × (hr) | Relative density (%) |
| Example 1A | hydrostatic pressing | 1.0 | pure oxygen | 760 | 1,050 × 2 | 99.3 |
| Example 2A | hydrostatic pressing | 1.5 | pure oxygen | 760 | 1,050 × 2 | 99.3 |
| Example 3A | hydrostatic pressing | 2.0 | pure oxygen | 760 | 1,050 × 2 | 99.5 |

TABLE 1-continued

|  | Production of green compact | | Sintering of green compact | | | Evaluation results |
| --- | --- | --- | --- | --- | --- | --- |
|  | Method of pressing | Pressure (ton/cm$^2$) | Sintering atmosphere | Pressure in sintering furnace (mmHg) | Temp. × Time (° C.) × (hr) | Relative density (%) |
| Example 4A | hydrostatic pressing | 2.0 | pure oxygen | 760 | 925 × 2 | 99.1 |
| Example 5A | hydrostatic pressing | 2.0 | pure oxygen | 760 | 950 × 2 | 99.2 |
| Example 6A | hydrostatic pressing | 2.0 | pure oxygen | 760 | 1,000 × 2 | 99.5 |
| Example 7A | hydrostatic pressing | 2.0 | pure oxygen | 760 | 1,250 × 2 | 99.6 |
| Example 8A | hydrostatic pressing | 2.0 | oxygen + Ar | 760 (Partial pressure of O$_2$:190) | 1,050 × 2 | 99.2 |
| Example 9A | hydrostatic pressing | 2.0 | oxygen + Ar | 760 (Partial pressure of O$_2$:380) | 1,050 × 2 | 99.4 |
| Example 10A | hydrostatic pressing | 2.0 | oxygen + Ar | 760 (Partial pressure of O$_2$:570) | 1,050 × 2 | 99.5 |
| Com. Example 1A | hydrostatic pressing | 0.5 | pure oxygen | 760 | 1,050 × 2 | 98.5 |
| Com. Example 2A | hydrostatic pressing | 1.0 | pure Ar | 760 | 1,050 × 2 | 98.0 |
| Com. Example 3A | hydrostatic pressing | 2.0 | atmospheric air | 760 | 1,050 × 2 | 99.1 |
| Com. Example 4A | hydrostatic pressing | 2.0 | pure oxygen | 760 | 900 × 2 | 97.8 |

As shown in Table 1, each of the sintered compacts manufactured in Examples 1A to 10A (sintered compacts of the first embodiment of the present invention) had high relative density.

Further, each of the sintered compacts which were manufactured by using green compacts which had been compressed at a pressure of 2 to 3 ton/cm$^2$ and then sintering the green compacts in an oxygen-containing atmosphere with a partial pressure of oxygen of 550 mmHg or higher at a sintering temperature of 1,000 to 1,250° C. had especially high relative density.

On the other hand, each of the sintered compacts manufactured in Comparative Examples 1A to 4A had low relative density.

Further, test pieces A and B (sintered compacts) in a sheet form having dimensions of 45 mm (L)×25 mm(W)×15 mm(H) were manufactured in the same manner as Example 3A and Comparative Example 3A, respectively.

In this regard, it is to be noted that the test piece A had transparent white color and the test piece B had opaque (milky) white color having no transparency.

For each of the test pieces A and B, characteristic evaluation was made as follows.

A light source in which light is emitted from an 85 W halogen lamp through optical fibers was prepared. The light emitted from the light source was measured with a colorimeter ("CS-100" manufactured by Minolta Co., Ltd.), and as a result the light had a luminance of 230,000 cd/m$^2$ and a chromaticity expressed by chromaticity coordinates (0.543, 0.4) on the CIE chromaticity diagram.

An area having a thickness of 15 mm of each of the test pieces A and B was irradiated with such light, and then the luminance of transmitted light through the test piece was measured with the colorimeter.

As a result, the luminance of transmitted light through the test piece A was 480 cd/m$^2$. On the other hand, the luminance of transmitted light through the test piece B was 63 cd/m$^2$.

From these results, it has been confirmed that the test piece A had higher transparency as compared with the test piece B.

Further, it was possible to visually check the condition of the inside of the test piece A, and as a result, occurrence of sintering flaws such as cracking, and contamination were not observed. On the other hand, it was difficult to visually check the condition of the inside of the test piece B because of the lack of transparency so that it was impossible to determine whether or not sintering flaws existed therein.

In this connection, test pieces were manufactured on the same conditions as Examples 1A, 2A, and 4A to 10A and Comparative Examples 1A, 2A and 4A, respectively, and characteristic evaluation was carried out for each of the test pieces in the same manner as described above. As a result, it has been confirmed that there is a correlation between the relative density of each of the sintered compacts manufactured in Examples 1A to 10A and Comparative Examples 1A to 4A and the result of the characteristic evaluation of each of the test pieces. That is, it has been confirmed that there is a tendency that transparency becomes higher as relative density increases.

As has been described above, according to the first embodiment of the sintered compact manufacturing method of the present invention, it is possible to obtain high-density sintered compacts.

Further, since such a sintered compact has high transparency, it is possible to easily detect the presence or absence of the occurrence of sintering flaws or the presence or absence of contamination inside the sintered compact.

Furthermore, by appropriately setting the manufacturing conditions of sintered compacts, it is possible for an obtained sintered compact to have higher relative density and higher transparency.

The sintered compact manufactured by the first embodiment of the sintered compact manufacturing method of the present invention can be suitably used as artificial bone such as a vertebral spacer or an auditory ossicle, dental implants and the like. Further, the sintered compact can also be suitably used as a material for a carrier for cell culture or a cell culture base since hydroxyapatite has high affinity with cells, proteins or the like.

Hereinbelow, a detailed description will be made with regard to a second embodiment of the sintered compact manufacturing method according to the present invention and a sintered compact manufactured by the method.

Here, examples of apatite to be used in the second embodiment include hydroxyapatite, fluorapatite, apatite obtained by substituting metal ions (e.g., Ni ion, Co ion, Mn ion or the like) for at least a part of calcium ions of hydroxyapatite or fluorapatite, and the like. They can be used alone or in combination of two or more. In this regard, it is to be noted that the following description will be made using hydroxyapatite as the representative of apatite.

Figure 2:
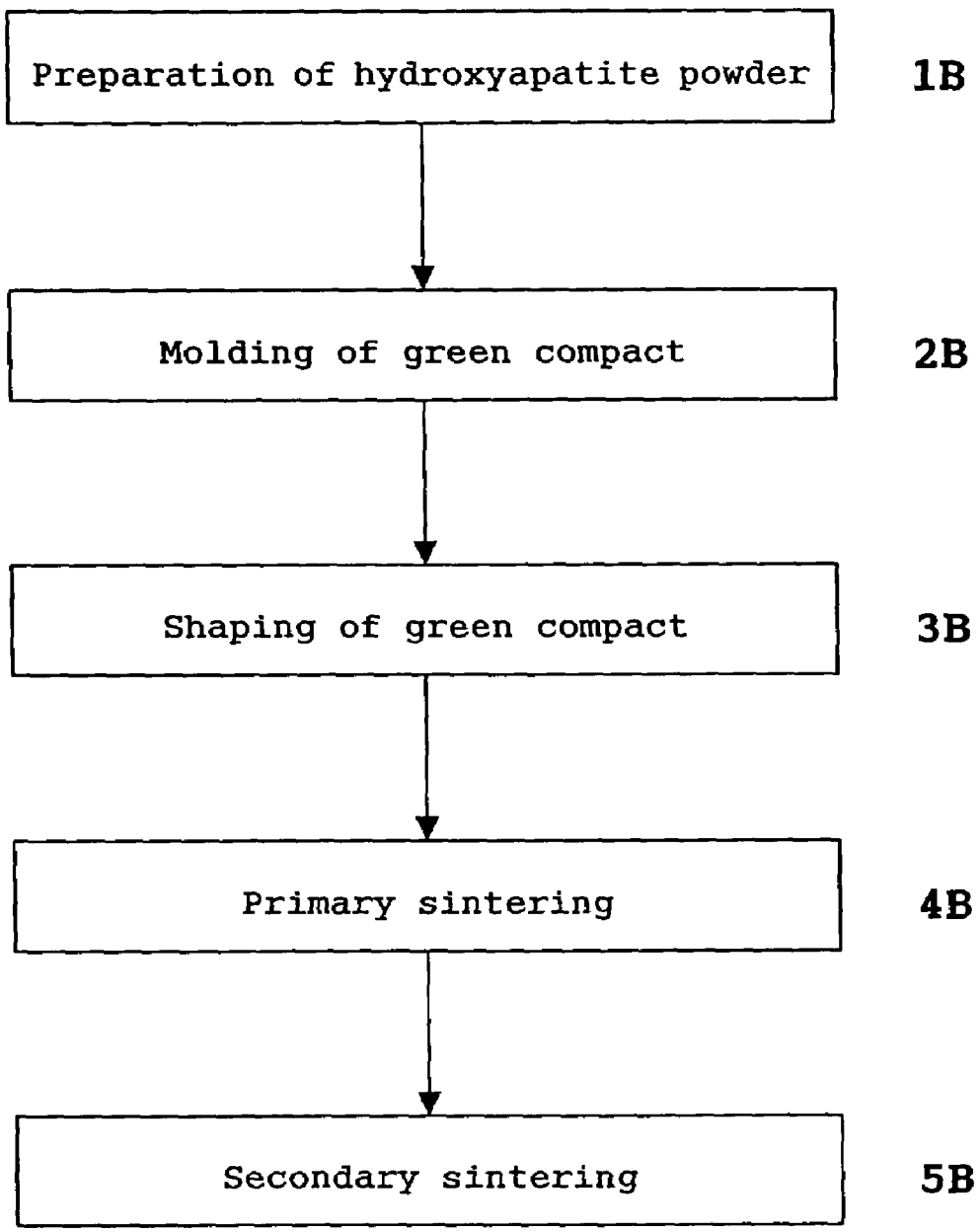
FIG. 2 is a step diagram which shows a second embodiment of the method for manufacturing a sintered compact according to the present invention.

FIG. 2 is a step diagram which shows the sintered compact manufacturing method of the second embodiment. The sintered compact manufacturing method shown in FIG. 2 comprises a step of preparing hydroxyapatite powder (step 1B), a step of molding a green compact (step 2B), a step of shaping the green compact into a desired form or size (step 3B), a primary sintering step (step 4B), and a secondary sintering step (step 5B). Each of the steps will now be described in order.

<1B> Preparation of Hydroxyapatite Powder

First, in the same manner as the first embodiment, a calcium source is reacted with a phosphoric acid source to synthesize hydroxyapatite (HAp). It is to be noted here that in this second embodiment the term "hydroxyapatite" means hydroxyapatite having a mole ratio of Ca to P (Ca/P) of 1.60 to 1.70.

Such hydroxyapatite can be synthesized by any method such as a wet synthesis method, a dry synthesis method or a hydrothermal synthesis method or the like. Among them, a wet synthesis method in which at least one of the calcium source and the phosphoric acid source is used in a liquid form is preferable. According to such a wet synthesis method, it is possible to easily and efficiently synthesize hydroxyapatite without the requirement for expensive manufacturing equipment.

In a case where the wet synthesis method is employed, calcium hydroxide, calcium oxide, calcium nitrate or the like can be used as a calcium source, for example. As for a phosphoric acid source, phosphoric acid, ammonium phosphate or the like can be used.

Among them, a calcium source containing calcium hydroxide or calcium oxide as a main ingredient, and a phosphoric acid source containing phosphoric acid as a main ingredient are preferable. By using such calcium source and phosphoric acid source, it is possible to more efficiently synthesize hydroxyapatite at a low cost.

A description will now be made with regard to a case where a calcium source containing calcium hydroxide or calcium oxide as a main ingredient and a phosphoric acid source containing phosphoric acid as a main ingredient are used.

In this case, hydroxyapatite (HAp) is synthesized by, for example, dropping a phosphoric acid solution ($H_3PO_4$) into a suspension of calcium hydroxide ($Ca(OH)_2$) or calcium oxide (CaO) within a vessel and then mixing them.

The reaction can be represented by the following equation (I) or (II).

$$10Ca(OH)_2 + 6H_3PO_4 \rightarrow 2Ca_5(PO_4)_3(OH) + 18H_2O \quad (I)$$

$$10CaO + 10H_2O + 6H_3PO_4 \rightarrow 2Ca_5(PO_4)_3(OH) + 18H_2O \quad (II)$$

If the reaction does not sufficiently proceed, an unreacted substance ($Ca(OH)_2$ or CaO) will exist as an impurity in a resultant mixture in a slurry state (hereinafter, simply referred to as a "slurry").

Further, when the reaction still goes on, another reaction represented by the following equation (III) occurs, and as a result tricalcium phosphate (TCP) is generated as a secondary reaction product.

$$3Ca_5(PO_4)_3(OH) + H_3PO_4 \rightarrow 5Ca_3(PO_4)_2 + 3H_2O \quad (III)$$

If this reaction occurs, tricalcium phosphate which is a secondary reaction product will exist in the resultant slurry as an impurity.

Hydroxyapatite powder is prepared from the slurry containing hydroxyapatite synthesized in such a manner. When the slurry hardly contains the impurities mentioned above, it is possible for a resultant sintered compact to have high density. Such a high-density sintered compact has high light permeability (translucency).

A description will now be made with regard to a preferred range of contents (concentrations) of each of tricalcium phosphate and unreacted substances ($Ca(OH)_2$, CaO) in the slurry.

(Tricalcium Phosphate)

The content (concentration) of tricalcium phosphate in the slurry is not limited to any specific value, but is preferably equal to or less than 0.1 wt %, and more preferably 0 wt %. When the content of tricalcium phosphate in the slurry lies within such a range, that is, by using the slurry containing less or no tricalcium phosphate, it is possible for a resultant sintered compact to have higher density.

Further, it is most suitable that the slurry satisfies the condition A described below.

The condition A: A part of the slurry is sampled and then subjected to compression molding at a molding pressure of 2 ton/cm² to form a sample green compact having a detection surface. The sample green compact is sintered in an atmospheric air at 1,200° C. for 2 hours to obtain a sample sintered compact, and then substances which exist on the detection surface (having a surface roughness Ra of 10 μm) of the sample sintered compact are analyzed by X-ray diffraction. At this time, the intensity of a peak derived from hydroxyapatite is the largest among obtained peaks and a peak derived from tricalcium phosphate is not observed.

Such an analytical method is based on the fact that in the sintering process described above, grain growth of hydroxyapatite occurs prior to that of the impurities due to the difference in their sintering rates, and as a result the impurities are excluded from a void between the grains and then deposited on the surface of the sample sintered compact (in particular, on the detection surface). Therefore, by analyzing the detection surface by means of the X-ray diffraction, it is possible to detect the presence or absence of the impurities. According to this analytical method, it is possible to determine whether or not the impurities exist in the slurry with high accuracy.

When the slurry satisfies the condition A, it is confirmed that the slurry does not contain tricalcium phosphate or even if the slurry contains tricalcium phosphate, the amount thereof is extremely small. Therefore, by using such a slurry, it is possible to obtain especially high-density sintered compacts.

(Unreacted Substance)

The content (concentration) of the unreacted substance in the slurry is not limited to any specific value, but is preferably equal to or less than 3 wt %, and more preferably in the range of about 0.025 to 1 wt %. Even if a relatively small amount of the unreacted substance such as calcium oxide exists in the slurry, calcium oxide has no effect on the sintered density of a resultant sintered compact as long as the amount of calcium oxide contained in the slurry is very small (Note that in a case where the unreacted substance is calcium hydroxide, calcium hydroxide is changed into calcium oxide due to sintering). Therefore such a condition as to the content of the unreacted substance is acceptable. If the content of the unreacted substance in the slurry exceeds the above upper limit value, there is a case where it becomes difficult to obtain high-density sintered compacts depending on conditions during sintering of green compacts which will be described later.

Further, it is also most suitable that the slurry satisfies the condition B described below.

The condition B: A part of the slurry is sampled and then dried at 200° C. to obtain a sample. The sample is sintered in an atmospheric air at 1,200° C. for 20 minutes to obtain a sintered sample, and then substances which exist in the sintered sample are analyzed by powder X-ray diffraction. At this time, when the intensity of a peak derived from hydroxyapatite is defined as X and the intensity of a peak derived from calcium oxide is defined as Y, X and Y satisfy the relation $Y/X<1/10$ (especially, $Y/X<1/100$).

As described above, according to such an analytical method, it is also possible to determine whether or not the impurities exist in the slurry with high accuracy. When the slurry satisfies the condition B, it is confirmed that the content of the unreacted substance in the slurry is extremely small. By using such a slurry, it is also possible to obtain especially high-density sintered compacts.

Further, at least one of the contents of the tricalcium phosphate and the unreacted substance in the slurry should lie within the range described above, but it is preferred that both of the contents of the tricalcium phosphate and the unreacted substance lie within the respective ranges described above. This makes it possible to obtain extremely high-density sintered compacts.

Next, hydroxyapatite powder (hereinafter, simply referred to as "powder") is prepared by, for example, spray drying the thus obtained slurry.

The mean particle size of the powder is not limited to any specific value, but is preferably equal to or less than 40 μm, and more preferably in the range of about 8 to 25 μm. By using powder having such a mean particle size, it is possible to obtain higher-density sintered compacts.

It is to be noted here that the obtained powder may be subjected to heat treatment under the condition of 500 to 800° C. for 2 to 6 hours, for example, and then milled using, for example, a jet mill or a turbo mill so that the powder has a mean particle size of about 6 to 20 μm (which is about 50 to 80% of a mean particle size before milling). By using such milled powder, it is possible to obtain more closely compacted green compacts.

<2B> Molding of Green Compact

Next, the thus obtained powder (or a powder compact which has been molded into a desired form in advance) is compacted by the application of pressure.

As for a method of applying pressure, any method such as isotropic pressing, pressing in only one direction (uniaxial direction) e.g., uniaxial pressing, or the like can be employed. Among them, isotropic pressing, especially hydrostatic pressing is preferable. By using such a method, it is possible for a resultant green compact to have uniform density, and as a result, a higher-density sintered compact can be obtained.

As for hydrostatic pressing, CIP (Cold Isostatic pressing) in which pressure is applied at a temperature of about 5 to 50° C. (preferably, about 10 to 30° C.) is suitably used. Since CIP has such advantages that it can be carried out with simple equipment and that a film (which will be described later) is not required to have heat resistance, CIP is practically useful as a technique for use in manufacturing industrial products. Alternatively, HIP (Hot Isostatic pressing) in which pressure is applied with heating (at 65° C. or higher, for example), or Hot press may be employed.

Specifically, in hydrostatic pressing, the powder enclosed with a liquid-proof film is placed in a hydrostatic pressing unit, and then hydrostatic pressure is applied. In the case of CIP, examples of a material of the film include: resin such as polyvinyl chloride, polyethylene, polypropylene and the like; and rubber such as natural rubber and isoprene rubber. The film can be formed by, for example, dipping or vacuum packing.

A pressure to be applied is 1 ton/cm$^2$ or higher, more preferably in the range of about 1 to 3 ton/cm$^2$, and even more preferably in the range of about 1.5 to 2.5 ton/cm$^2$. If the pressure is too low, there is a case where a sufficient effect by pressing (especially, uniformity in density) can not be expected. On the other hand, even if the pressure is increased so as to exceed the above upper limit value, an improved effect can not be obtained. Further, use of such an increased pressure requires large-scale equipment, thus resulting in an increased equipment cost.

The green compact obtained by applying pressure in such a manner described above can have high and uniform density. When such a green compact is subjected to primary sintering in a manner as will be described later, the green compact is uniformly shrunk. Therefore, an obtained sintered compact has high dimensional accuracy and uniform density.

Further, such uniform density suppresses the occurrence of sintering flaws such as cracking, chipping and the like in the sintered compact, and therefore such a sintered compact is hard to be damaged (that is, it has excellent mechanical strength). In this connection, the film covering the surface of the powder is removed by a predetermined method after pressing.

<3B> Shaping of Green Compact

Next, the thus obtained green compact is shaped into a desired form or size, as necessary.

The green compact is shaped by, for example, subjecting it to a predetermined machine working. Examples of the machine working include cutting, grinding, polishing and the like, and they can be carried out singly or in combination of two or more.

Since the hardness of the green compact itself is very low as compared with that of a finally obtained sintered compact, it is possible to easily carry out the machine working or the like onto the green compact. In particular, the green compact has advantages in that machine working can be carried out with low hardness tools and it takes shorter time to complete machine working.

<4B> Primary Sintering

The thus obtained green compact is subjected to primary sintering in a sintering furnace having an oxygen-containing atmosphere in which 50 vol % or more of a gas existing in the sintering furnace is occupied by oxygen, to thereby obtain a sintered compact.

The present inventors have conducted extensive research, and as a result found that by sintering the green compact in an oxygen-containing atmosphere in which 50 vol % or more (preferably, 75 vol % or more) of a gas existing in a sintering furnace is occupied by oxygen, it is possible to obtain a sintered compact having especially high density and high light permeability.

A typical example of such an oxygen-containing atmosphere (sintering atmosphere) includes a pure oxygen atmosphere. Alternatively, a mixed gas of oxygen and other gases (in particular, a mixed gas mainly containing oxygen) may be used as the oxygen-containing atmosphere.

The partial pressure of oxygen in the oxygen-containing atmosphere (in the case of a pure oxygen atmosphere, the partial pressure of oxygen means a pressure in the sintering furnace) is preferably equal to or higher than 380 mmHg, and more preferably equal to or higher than 550 mmHg. By setting the partial pressure of oxygen to the above range, it is possible for an obtained sintered compact to have higher relative density and higher light permeability.

Further, the pressure of the oxygen-containing atmosphere (pressure in the sintering furnace) is preferably equal to or less than 900 mmHg, and more preferably equal to or less than 600 mmHg. By setting the pressure of the oxygen-containing atmosphere to the above range, it is possible to further increase the light transmittance of the sintered compact. In a case where sintering is carried out under reduced pressure, oxygen should occupy 50 vol % or more of a gas in a space where sintering is carried out.

In this connection, under atmospheric pressure, by increasing the volume (concentration) of oxygen in the oxygen-containing atmosphere (sintering atmosphere), the partial pressure of oxygen in the oxygen-containing atmosphere becomes high.

Further, the present inventors have also found that by sintering the green compact in such an oxygen-containing atmosphere whose concentration of oxygen is high, it is possible to carry out primary sintering at a relatively low temperature (sintering temperature). Further, they have also found that in this case the green compact can be sintered while the grain growth of hydroxyapatite is being suppressed and as a result sintered compacts having higher density and higher light permeability can be obtained.

Furthermore, sintering of green compacts at a relatively low temperature also has advantages in that sintering time, energy consumed for sintering and the cost of a heating element used in a sintering furnace can be reduced.

A temperature during primary sintering (sintering temperature) is preferably in the range of 850 to 1,350° C., and more preferably in the range of about 950 to 1,250° C. If the sintering temperature is too low, there is a case that the green compact is not efficiently sintered.

A period of time over which the sintering temperature is being held (sintering time) is preferably in the range of about 30 minutes to 8 hours, and is more preferably in the range of about 2 to 4 hours.

The thus obtained sintered compact has high density and high light permeability. Specifically, such a sintered compact allows light having wavelengths equal to or longer than those of visible light to pass therethrough.

<5B> Secondary Sintering

Next, the thus obtained sintered compact is subjected to secondary sintering in, for example, an atmosphere with low level of activity in the sintering furnace.

The present inventors have conducted extensive research to obtain a sintered compact which allows light having various wavelengths (light having wavelengths shorter than those of visible light) to pass therethrough, and as a result found that by again sintering the sintered compact (secondary sintering) in an atmosphere with low level of activity, it becomes possible for an obtained sintered compact to allow light having wavelengths shorter than those of visible light to pass therethrough.

The atmosphere with low level of activity is not limited to any specific one as long as the main constituent thereof does not substantially react with hydroxyapatite (apatite). For example, inert gas atmosphere such as nitrogen gas atmosphere, argon gas atmosphere, helium gas atmosphere, or neon gas atmosphere is preferred, because each of the gases has extremely low reactivity to hydroxyapatite (apatite).

Also, these gases may be used in combination, as necessary.

A temperature during secondary sintering (sintering temperature) is preferably in the range of about 1,000 to 1,350° C., and more preferably in the range of about 1,100 to 1,250° C. If the temperature during the secondary sintering is less than the above lower limit value, there is a possibility that the effect described above can not be sufficiently obtained. On the other hand, even if the temperature during the secondary sintering is increased so as to exceed the above upper limit value, an effect exceeding the effect described above can not be obtained. Further, there is a possibility that hydroxyapatite will be decomposed by heat.

A period of time over which the sintering temperature is being held (sintering time) is preferably in the range of about 30 minutes to 8 hours, and is more preferably in the range of about 2 to 4 hours.

The pressure of an atmosphere with low level of activity (pressure in the sintering furnace) is preferably in the range of about 3 to 900 mmHg, and more preferably in the range of about 5 to 800 mmHg. Here, the required amount of oxygen existing in the sintering atmosphere is very small.

It is to be noted here that the relative density of the sintered compact to be subjected to the secondary sintering in the process <5B> described above is preferably 99% or higher (in particular, 99.5% or higher). By using such a sintered compact, it is possible for an obtained sintered compact to allow light having wavelengths shorter than those of visible light to pass therethrough more reliably.

The process <5B> may be carried out in a sintering furnace which is different from that used in the process <4B>, but it is preferred that both processes <4B> and <5B> are carried out in the same sintering furnace. In this case, the sintering atmosphere is changed between the processes <4B> and <5B>. By carrying out the processes <4B> and <5B> in the same sintering furnace, it is possible to carry out these two processes (sintering) successively without taking an object to be subjected to sintering out of the sintering furnace, thus resulting in a reduction in time required to manufacture sintered compacts.

Through the processes described above, a sintered compact of the second embodiment of the present invention can be obtained.

Since the sintered compact of the second embodiment has high density, mechanical strength thereof is extremely high. Therefore, the sintered compact manufactured by the second embodiment of the sintered compact manufacturing method of the present invention can be suitably used as a biomaterial for artificial bone such as a vertebral spacer, an auditory ossicle and the like, dental implants, and the like. Further, the sintered compact manufactured by the second embodiment can also be suitably used as a material for a carrier for cell culture or a cell culture base since hydroxyapatite has high affinity with cells, proteins or the like.

Further, since the sintered compact manufactured by the second embodiment has high light permeability, it can be suitably used as a carrier for cell culture (container), a cell culture base, a container for analysis (cell), or the like.

In a case where the sintered compact manufactured by this second embodiment is used as a carrier for cell culture (container), the condition of cells which adhere to and grow on the cell culture carrier can be observed by an optical method (a method using an optical microscope, for example). Such a method has an advantage in that it is possible to observe cells relatively easily without the requirement for large-scale equipment.

Further, in a case where the sintered compact manufactured by this second embodiment is used as a container for cell culture or a container for analysis, since the sintered compact allows light having wavelengths in the range of ultraviolet rays to pass therethrough, there is an advantage in that the concentration of protein in a solution in the container can be easily measured by a simple method using ultraviolet rays (with wavelengths of about 280 to 300 nm). In this case, it is particularly preferred that the sintered compact of this second embodiment has the following characteristic.

Specifically, the characteristic is that when a sheet-shaped test piece (sintered compact) having a thickness of 0.5 mm is irradiated with light of wavelength of 300 nm, the transmittance of the light passing through the test piece is 10% or higher (in particular, 15% or higher).

Here, the reason why such a test piece is used is the same as that described above in connection with the first embodiment. Namely, the shape and size of the sintered compact to be practically used is appropriately set according to its purpose of use, that is, practically used sintered compacts have various shapes and sizes. Therefore, even if light transmittances through the sintered compacts having various shapes and sizes are measured under the same condition, evaluations can not be made based on the same standard due to their various shapes and sizes. Therefore, a test piece having the above characteristic is made according to the above-described sintered compact manufacturing method. By preparing such a test piece, if a sintered compact to be practically used is manufactured under the same conditions as those for the test piece, it is possible to consider that the sintered compact has a similar characteristic to the test piece.

Further, since the test piece having the characteristic described above is considered to allow light having wavelengths shorter than those of visible light to pass through the test piece efficiently, a sintered compact manufactured under the same conditions as those for the test piece is also believed to allow light having wavelengths shorter than those of visible light to pass through the sintered compact efficiently.

Although the sintered compact manufacturing method and the sintered compact of the second embodiment of the present invention have been described in the above, the present invention is not limited thereto.

For example, the sintered compact manufacturing method of the second embodiment may include a preliminary step coming before the step 1B, an intermediate step coming between the steps 1B to 5B, or a post step coming after the step 5B (step of carrying out surface treatment onto the sintered compact, for example).

EXAMPLE

Next, actual examples of the sintered compact manufacturing method of the second embodiment of the present invention will be described.

<Manufacture of Sintered Compact>

Sintered compacts of Examples 1B to 3B and Comparative Examples 1B to 3B were manufactured as follows.

Example 1B

<1> First, 140 g of calcium hydroxide was dispersed in 6 liters of pure water, and then an aqueous phosphoric acid solution whose concentration of phosphoric acid was 2 wt % was dropped into the pure water in which calcium hydroxide was dispersed. They were sufficiently mixed with stirring to synthesize hydroxyapatite, and as a result a slurry containing hydroxyapatite was obtained.

Next, the obtained slurry was spray dried using a spray dryer to obtain hydroxyapatite powder having a mean particle size of 14 μm.

At that time, a part of the slurry was sampled, and was then subjected to compression molding at a molding pressure of 2 ton/cm$^2$ to form a sample green compact having a detection surface. The thus obtained sample green compact was sintered in an atmospheric air at 1,200° C. for 2 hours to obtain a sample sintered compact, and then substances existing on the detection surface (having a surface roughness Ra of 10 μm) of the sample sintered compact were analyzed by X-ray diffraction. In this connection, the sample had a diameter of 15 mm and a height of 8 mm.

As a result of analysis, a peak derived from tricalcium phosphate (TCP) was not observed.

Further, a part of the slurry was again sampled and then dried at 200° C. to obtain a sample. Thereafter, the obtained sample was sintered in an atmospheric air at 1,200° C. for 20 minutes, and then the sintered sample was analyzed by a powder X-ray diffraction. As a result, the intensity of a peak derived from calcium oxide (CaO) was 1/250 of that derived from hydroxyapatite (HAp).

The thus obtained hydroxyapatite powder was subjected to heat treatment under the condition of 600° C. for 4 hours, and was then milled using a jet mill. In this way, hydroxyapatite powder having a mean particle size of 13 μm was obtained.

<2> Next, the thus obtained hydroxyapatite powder was compressed into a disk-like shape by the use of a compression molding machine, and thereafter the powder formed into the disk-like shape was put into a plastic bag and vacuum-sealed. Then, a hydrostatic pressure of 1 ton/cm$^2$ was applied to the disk shaped powder in the plastic bag under room temperature (24° C.), to thereby obtain a disk shaped green compact having a diameter of 28 mm and a thickness of 1 mm.

<3> Next, cutting (machine working) was carried out onto the green compact by the use of a diamond cutter so that the disk shaped green compact had a diameter of 25 mm and a thickness of 0.8 mm.

<4> Next, the thus obtained green compact was sintered (primary sintering) in a sintering furnace to obtain a sintered compact. In this regard, it is to be noted that sintering was carried out in a pure oxygen atmosphere (sintering atmosphere) at 1,200° C. for 2 hours. At this time, a pressure in the sintering furnace was set to 76 mmHg.

Further, the relative density of the obtained sintered compact (sintered compact after primary sintering) was 99.6%. The relative density of the sintered compact was determined based on its volume defined by external dimensions and its weight, in consideration of specific gravity.

<5> Next, the sintered compact was again sintered (secondary sintering) in the same sintering furnace as that used in the process <4> described above.

In this regard, it is to be noted that sintering was carried out in an argon gas atmosphere (sintering atmosphere) at 1,200° C. for 2 hours. At this time, a pressure in the sintering furnace was set to 380 mmHg.

In this connection, the relative density of the sintered compact was 99.8%.

<6> Next, optical polishing was carried out onto both surfaces of the sintered compact so that the sintered compact had a diameter of 20 mm and a thickness of 0.5 mm.

Example 2B

A sintered compact was manufactured in the same manner as Example 1B except that the pressure in the sintering furnace was changed to 350 mmHg in the process <4> described above and that the sintering temperature in the process <5> described above was changed to 1,100° C. In this connection, the relative density of the sintered compact after primary sintering was 99.6% and the relative density of the sintered compact after the secondary sintering was 99.7%.

Example 3B

A sintered compact was manufactured in the same manner as Example 1B except that the sintering temperature in the process <4> described above was changed to 1,050° C. and the pressure in the sintering furnace was changed to 760 mmHg., and that the sintering temperature in the process <5> described above was changed to 1,050° C. In this connection, the relative density of the sintered compact after the primary sintering was 99.5% and the relative density of the sintered compact after the secondary sintering was 99.5%.

Comparative Example 1B

A sintered compact was manufactured in the same manner as Example 3B except that the process <5> described above was omitted. In this connection, the relative density of the obtained sintered compact was 99.5%.

Comparative Example 2B

A sintered compact was manufactured in the same manner as Example 1B except that the process <4> described above was omitted. In this connection, the relative density of the obtained sintered compact was 99.0%.

Comparative Example 3B

A sintered compact was manufactured in the same manner as Example 1B except that the green compact was sintered in an atmospheric air at 1 atom and 1,200° C. for 2 hours instead of carrying out the processes <4> and <5>. In this connection, the relative density of the obtained sintered compact was 99.1%.

Evaluation

1. Measurement of Wavelengths of Light that is Allowed to Pass Through each Sintered Compact For each of the sintered compacts manufactured in Examples 1B to 3B and Comparative Examples 1B to 3B, measurement of wavelengths of light that is allowed to pass therethrough was made. In this measurement, a spectrophotometer "U-4000" made by Hitachi, Ltd. was used.

2. Measurement of Light Transmittance

Each of the sintered compacts manufactured in Examples 1B to 3B and Comparative Examples 1B to 3B was irradiated with light of wavelength of 300 nm, and then the light transmittance thereof at that time was measured. The evaluation results and manufacturing conditions of the sintered compacts in each of Examples and Comparative Examples are shown in Table 2.

when the sintered compact was irradiated with light of wavelength of 300 nm was high.

On the other hand, each of the sintered compacts manufactured in Comparative Examples 1B to 3B did not allow light having wavelengths shorter than 295 nm to pass therethrough. Further, each of the sintered compacts hardly allowed light of wavelength of 300 nm to pass therethrough.

Next, a detailed description will be made with regard to preferred embodiments of a cell culture base and a method for manufacturing the cell culture base according to the present invention.

FIRST EMBODIMENT

Figure 3:
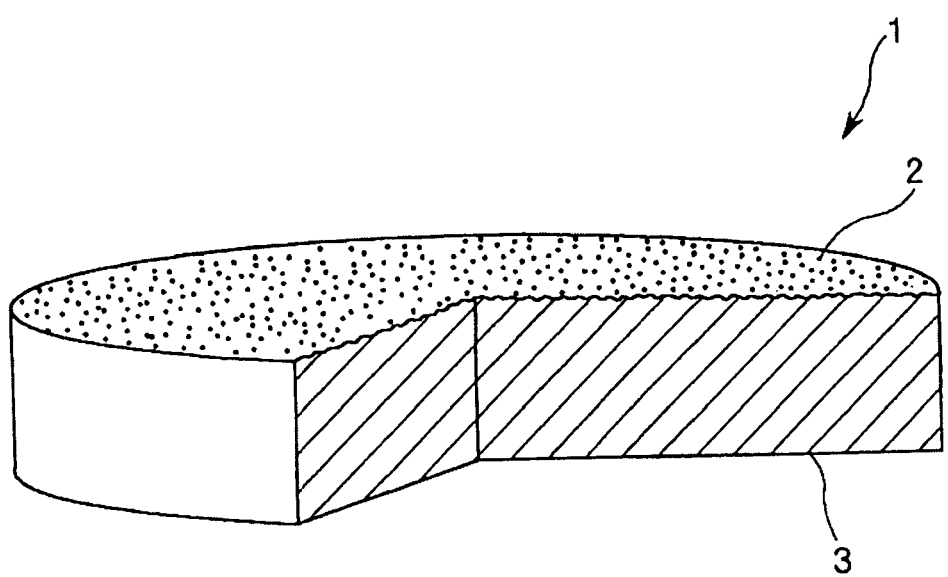
FIG. 3 is a perspective view which shows a first embodiment of a cell culture base of the present invention, in which the present invention is applied to a pellet for cell culture.
Figure 4:
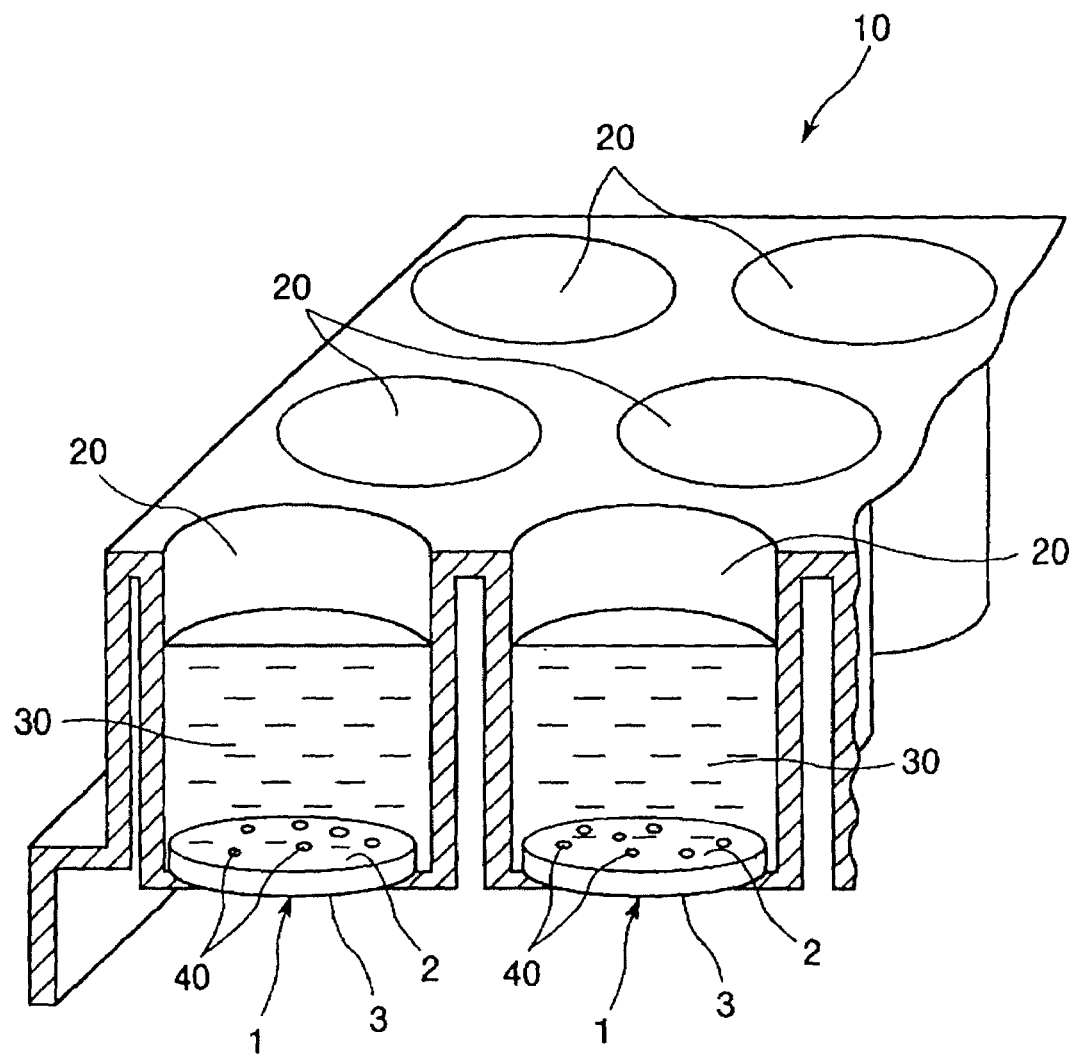
FIG. 4 is an illustration (partially sectioned perspective view) for explaining how to use the pellet for cell culture shown in FIG. 3.
Figure 5:
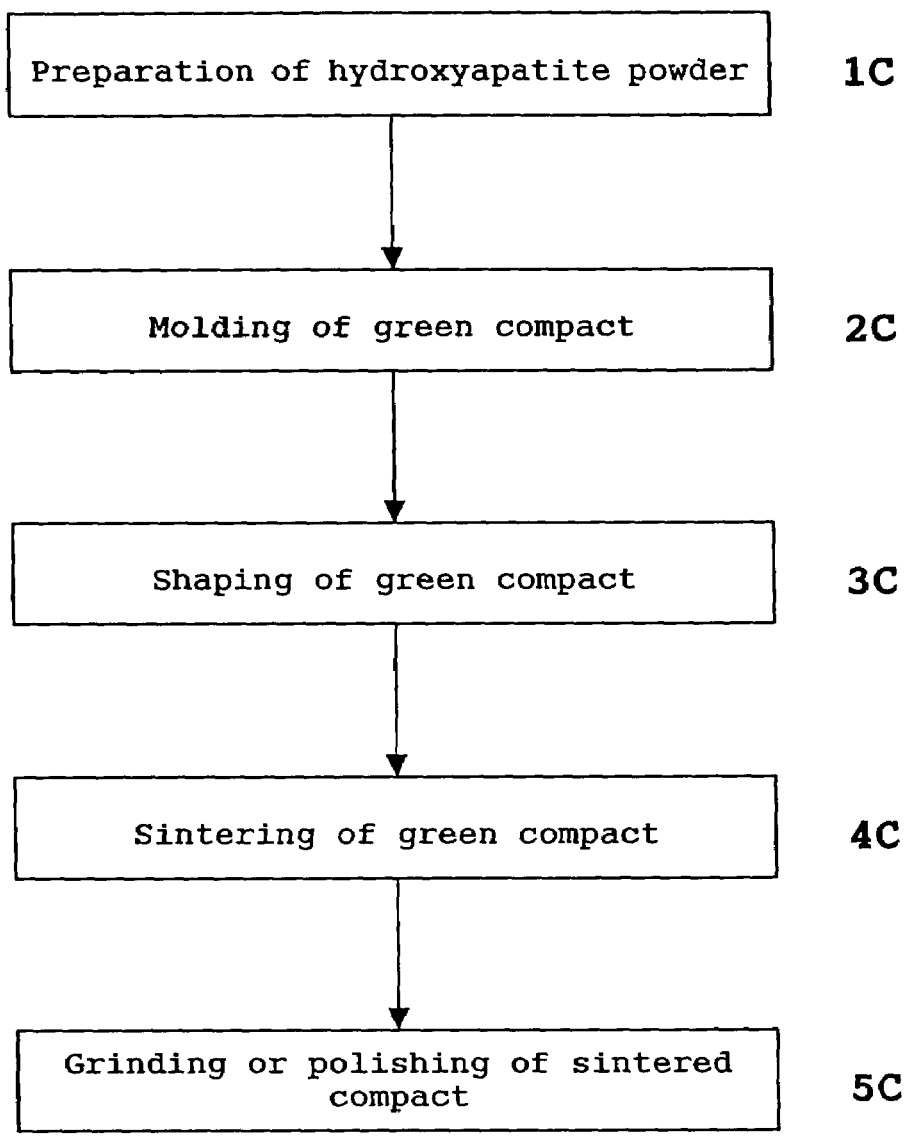
FIG. 5 is a step diagram which shows a method for manufacturing the pellet for cell culture shown in FIG. 3.

FIG. 3 is a perspective view which shows a first embodiment of the cell culture base of the present invention, in which the present invention is applied to a pellet for cell culture, FIG. 4 is an illustration (partially sectioned perspective view) for explaining how to use the pellet for cell culture shown in FIG. 3, and FIG. 5 is a step diagram which shows a method for manufacturing the pellet for cell culture shown in FIG. 3. In this connection, in the following description, the upper side and the lower side in FIGS. 3 to 5 will be referred to as "top" and "bottom", respectively.

A pellet for cell culture 1 shown in FIG. 3 is used for culturing cells by allowing various kinds of cells to adhere thereto. The pellet for cell culture 1 is mainly composed of a calcium phosphate based compound as a whole, and is substantially formed into a disk-like shape.

In a case where the pellet for cell culture 1 is formed into the disk-like shape, the diameter thereof is preferably in the range of about 0.5 to 200 mm, more preferably in the range of about 0.5 to 100 mm, and even more preferably in the range of about 0.5 to 35 mm.

The pellet for cell culture 1 allows various kinds of cells (anchorage-dependent cells) to adhere to one surface thereof (that is a top surface in FIG. 3) and grow. Hereinafter, the top surface of the pellet for cell culture 1 shown in FIG. 3 is referred to as a "cell adhesion surface (cell base surface) 2".

The degree of adhesion of cells to the pellet for cell culture 1 and the degree of growth of cells (the condition of cells) can be observed by various methods, however, it is preferred that

TABLE 2

| | | Primary sintering | | | Secondary sintering | | Evaluation results | |
| --- | --- | --- | --- | --- | --- | --- | --- | --- |
| | | Pressure | | | Pressure | | | |
| | Atmosphere | in sintering furnace (mmHg) | Temp. × Time (° C.) × (hr) | Atmosphere | in sintering furnace (mmHg) | Temp. × Time (° C.) × (hr) | Wavelengths allowed to pass through (nm) | Transmittance (%) |
| Example 1B | pure oxygen | 76 | 1,200 × 2 | pure argon | 380 | 1,200 × 2 | 275 or higher | 50 |
| Example 2B | pure oxygen | 350 | 1,200 × 2 | pure argon | 380 | 1,100 × 2 | 275 or higher | 25 |
| Example 3B | pure oxygen | 760 | 1,050 × 2 | pure argon | 380 | 1,050 × 2 | 275 or higher | 15 |
| Com. Example 1B | pure oxygen | 760 | 1,050 × 2 | — | | | 325 or higher | 0 |
| Com. Example 2B | | — | | pure argon | 380 | 1,200 × 2 | 295 or higher | 2 |
| Com. Example 3B | | — | | atmospheric air | 760 | 1,200 × 2 | 340 or higher | 0 |

As shown in Table 2, each of the sintered compacts manufactured in Examples 1B to 3B (that is, the sintered compacts of the second embodiment) allows light having wavelengths of 275 nm or longer to pass therethrough. Further, the light transmittance of each of the sintered compacts at the time they are observed in a state that light is being allowed to pass through the pellet for cell culture 1. According to such a method, it is possible to relatively easily observe the condition of cells without the requirement for large-scale equipment.

In this case, it is particularly preferred that the condition of cells is observed from the side of another surface which is opposite to the cell adhesion surface 2 in a state that the pellet for cell culture 1 is being irradiated with light from the side of the cell adhesion surface 2. By doing so, it is possible to more properly observe a state in which the cells adhere to the cell adhesion surface 2 of the pellet for cell culture 1. Further, in recent years, regenerative medical techniques are widely practically utilized. In accompanying with this, there is a demand to observe the relation between a calcium phosphate based compound such as hydroxyapatite or tricalcium phosphate and various kinds of cells. For this purpose, such a transparent (translucent) pellet for cell culture 1 is practically useful.

As described above, the condition of cells on the pellet for cell culture 1 is observed from the side of another surface (that is, the side of the bottom surface in FIG. 3) which is opposite to the cell adhesion surface 2 in a state that the pellet for cell culture 1 is being irradiated with light from the side of the cell adhesion surface 2 (that is, the side of the top surface in FIG. 3). Hereinafter, the bottom surface (another surface) of the pellet for cell culture 1 shown in FIG. 3 is referred to as an "observation surface 3".

Also as described above, since the pellet for cell culture 1 is mainly composed of a calcium phosphate based compound as a whole, it is possible to culture cells under conditions similar to those in a living body. Further, it is also possible to solve the existing problems, that is, to properly evaluate the affinity of various cells with bone and to transplant the pellet for cell culture 1 itself with the cells being cultured on the cell adhesion surface 2 thereof into a living body after the completion of the cell culture.

The calcium phosphate based compound is not limited to any specific one, and various kinds of compounds can be used as long as the mole ratio of Ca to P (Ca/P) lies in the range of 1.0 to 2.0. Examples of the calcium phosphate based compound include hydroxyapatite, tricalcium phosphate, dicalcium phosphate, fluorapatite and the like, and they can be used singly or in combination of two or more.

Among them, a calcium phosphate based compound containing as a main ingredient hydroxyapatite or tricalcium phosphate is preferred. Since the former is the main ingredient of bone and the latter is close to the ingredient of bone, it is possible to more properly determine the affinity of various kinds of cells with bone.

As described above, since the condition of cells is preferably observed in a state that light is being allowed to pass through the pellet for cell culture 1, it is preferred that the transparency of the pellet for cell culture 1 is increased as high as possible.

From the viewpoint, the present inventors have conducted extensive research, and as a result found that the transparency of the pellet for cell culture 1 depends on the relative density of the pellet for cell culture 1 (that is, the transparency of the pellet for cell culture 1 increases with increase in the relative density thereof).

That is, the feature of the present invention is that the pellet for cell culture 1 is made to be highly dense. Therefore, the pellet for cell culture 1 can have required transparency to observe the condition of cells.

The degree of the density of the pellet for cell culture 1 can be determined using the porosity thereof as an index. Specifically, the porosity of the pellet for cell culture 1 is preferably equal to or less than 1%, and more preferably equal to or less than 0.6%. By setting the porosity of the pellet for cell culture 1 to the above range, it is possible to further increase the transparency of the pellet for cell culture 1.

Further, the average thickness of the pellet for cell culture 1 is preferably in the range of about 0.1 to 3 mm, and more preferably in the range of about 0.2 to 1.5 mm. By setting the average thickness of the pellet for cell culture 1 to the above range, it is possible for the pellet for cell culture 1 to have sufficiently high transparency without decrease in the strength of the pellet for cell culture 1.

A preferred degree of the transparency of the pellet for cell culture 1 is as follows, for example. Specifically, at the time when light of wavelength of 600 nm is allowed to pass through the pellet for cell culture 1 having an average thickness of 1 mm in the thickness direction thereof, the transmittance of the light passing through the pellet for cell culture 1 is preferably equal to or more than 1.5%, and more preferably equal to or more than 2%. By setting the transmittance to the above range, it is possible to more properly observe the condition of cells.

As shown in FIG. 3, the pellet for cell culture 1 has the cell adhesion surface 2 which provides a rough surface and the observation surface 3 which provides a smooth surface. This makes it possible for cells to easily and reliably adhere to the cell adhesion surface 2. In addition, since light passing through the pellet for cell culture 1 is prevented from being scattered at the observation surface 3 in observing the condition of cells due to its smooth surface, it is possible to more properly observe the condition of cells.

Further, it is preferred that the surface roughness of the cell adhesion surface 2 is not extremely large. Specifically, the rough surface is preferably a surface obtained by grinding it using a grinding material containing particles having an average particle size of about 5 to 30 μm (preferably about 5 to 25 μm), or a surface having substantially the same surface roughness as that obtained by such grinding. Such a rough surface can further increase the rate of adhesion of cells to the cell adhesion surface 2 as well as prevent irradiated light from being scattered at the cell adhesion surface 2 in observing the condition of cells so that it is possible to observe the condition of cells without difficulty.

On the other hand, it is preferred that the surface roughness of the observation surface 3 is as small as possible. Specifically, the smooth surface is preferably a surface obtained by polishing it using a polishing material containing particles having an average particle size of 1 μm or less (preferably, 0.8 μm or less) (that is, mirror polishing), or a surface having substantially the same surface roughness as that obtained by such polishing. Such a smooth surface makes it possible to more reliably prevent the scattering of light at the observation surface 3. Hereinafter, such a smooth surface obtained by mirror polishing is referred to as a "specular surface".

As for particles (abrasive grains) used in the grinding material and polishing material described above, particles (fine particles) of diamond, alumina, silica, ceric oxide, boron nitride, iron red, or the like can be mentioned, for example.

It is to be noted here that the pellet for cell culture 1 may have a structure different from that shown in FIG. 3. Specifically, both of the cell adhesion surface 2 and the observation surface 3 may provide rough surfaces, both of the cell adhesion surface 2 and the observation surface 3 may provide smooth surfaces, or both of the cell adhesion surface 2 and the observation surface 3 may provide specular surfaces.

When both the cell adhesion surface 2 and the observation surface 3 have the same surface property, users do not have to distinguish between the cell adhesion surface 2 and the observation surface 3 in use, which is advantageous to users.

In addition, in a case where both of the cell adhesion surface 2 and the observation surface 3 provide smooth surfaces (in particular, smooth surfaces which have not been subjected to mirror polishing), complicated operations for obtaining a rough surface or a specular surface can be omitted, thus resulting in a reduction in the manufacturing cost of the pellets for cell culture 1. In a case where both of the cell adhesion surface 2 and the observation surface 3 provide smooth surfaces (in particular, specular surfaces), there is an advantage that light transmittance in observing the condition of cells can be further increased.

The pellet for cell culture 1 described above is to be used with a plate 10 shown in FIG. 4, for example.

Hereinbelow, a description will be made with regard to one example of a method how to use the pellet for cell culture 1 (a method for culturing cells) with reference to FIG. 4.

The plate 10 shown in FIG. 4 has a plurality of wells 20 which can accommodate the pellets for cell culture 1, respectively. The inner diameter of each well 20 is set to be slightly larger than the diameter of the pellet for cell culture 1. Therefore, it is possible to easily put the pellet for cell culture 1 into the well 20 and take out it from the well 20.

First, the pellet for cell culture 1 is put into the well 20, and a culture medium 30 and cells 40 to be cultured are also supplied into the well 20 to culture the cells 40. The cells 40 adhere to the cell adhesion surface 2 of the pellet for cell culture 1 and grow thereon.

The culture medium 30 is appropriately selected depending on the types or the like of the cells 40 to be cultured, and is not limited to any specific one. Examples of the culture medium 30 include MEM, αMEM, Dulbecco's MEM, BME, MCDB-104 medium and the like.

In this regard, it is to be noted that additives such as serum, serum protein e.g., albumin, various kinds of vitamins, various kinds of amino acids, salts, and the like may be added to the culture medium 30, as necessary.

Further, the temperature of the culture medium (incubation temperature) is also appropriately set depending on the types of cells 40 to be cultured, and is not limited to any specific value. In general, it is set to about 20 to 40° C., and is preferably set to about 25 to 37° C.

Next, after cultivation is complete, the pellet for cell culture 1 is taken out of the well 20 of the plate 10, and then the cells 40 are subjected to a predetermined treatment (staining or the like, for example).

Thereafter, the condition of the cells 40 is observed from the side of the observation surface 3 in a state that the pellet for cell culture 1 is being irradiated with light from the side of the cell adhesion surface 2, for example. Such observation can be carried out with naked eyes or an optical microscope, for example.

In a case where the plate 10 is substantially transparent (transparent and colorless, transparent colored, or translucent), it is also possible to observe the cells 40 in a state that the pellet for cell culture 1 is being accommodated in the well 20, that is, without taking the pellet out of the well 20.

Hereinbelow, the method for manufacturing a pellet for cell culture (cell culture base) 1 will be described with reference to FIG. 5. In this connection, the following description will be made based on one example where hydroxyapatite is used as a calcium phosphate based compound.

The method for manufacturing the pellet for cell culture shown in FIG. 5 comprises a step of preparing hydroxyapatite powder (step 1C), a step of molding a green compact (step 2C), a step of shaping the green compact into a desired form or size (step 3C), a step of sintering the green compact to obtain a sintered compact (step 4C), and a step of grinding or polishing the sintered compact (step 5C). Hereinbelow, each of the steps will be described in this order.

<1C> Preparation of Hydroxyapatite Powder

First, in the same manner as the first and second embodiments of the sintered compact manufacturing method of the present invention described above, a calcium source is reacted with a phosphoric acid source to synthesize hydroxyapatite (HAp). It is to be noted here that in this embodiment the term "hydroxyapatite" means hydroxyapatite having a mole ratio of Ca to P (Ca/P) of 1.60 to 1.70.

Such hydroxyapatite can be synthesized by any method, such as a wet synthesis method, a dry synthesis method or a hydrothermal synthesis method or the like. Among them, a wet synthesis method in which at least one of the calcium source and the phosphoric acid source is used in a liquid form is preferable. According to such a wet synthesis method, it is possible to easily and efficiently synthesize hydroxyapatite without the requirement for expensive manufacturing equipment.

In a case where the wet synthesis method is employed, calcium hydroxide, calcium oxide, calcium nitrate or the like can be used as a calcium source, for example. As for a phosphoric acid source, phosphoric acid, ammonium phosphate or the like can be used. Among them, a calcium source containing calcium hydroxide or calcium oxide as a main ingredient, and a phosphoric acid source containing phosphoric acid as a main ingredient are preferable. By using such calcium source and phosphoric acid source, it is possible to more efficiently synthesize hydroxyapatite at a low cost.

A description will now be made with regard to a case where a calcium source containing calcium hydroxide or calcium oxide as a main ingredient and a phosphoric acid source containing phosphoric acid as a main ingredient are used.

In this case, hydroxyapatite (HAp) is synthesized by, for example, dropping a phosphoric acid solution ($H_3PO_4$) into a suspension of calcium hydroxide ($Ca(OH)_2$) or calcium oxide (CaO) in a vessel and then mixing them.

The reaction can be represented by the following equation (I) or (II).

$$10Ca(OH)_2 + 6H_3PO_4 \rightarrow 2Ca_5(PO_4)_3(OH) + 18H_2O \quad (I)$$

$$10CaO + 10H_2O + 6H_3PO_4 \rightarrow 2Ca_5(PO_4)_3(OH) + 18H_2O \quad (II)$$

If the reaction does not sufficiently proceed, an unreacted substance ($Ca(OH)_2$ or CaO) will exist as an impurity in a resultant mixture in a slurry state (hereinafter, simply referred to as a "slurry").

Further, when the reaction still goes on, another reaction represented by the following equation (III) occurs, and as a result tricalcium phosphate (TCP) is generated as a secondary reaction product.

$$3Ca_5(PO_4)_3(OH) + H_3PO_4 \rightarrow 5Ca_3(PO_4)_2 + 3H_2O \quad (III)$$

If this reaction occurs, tricalcium phosphate which is a secondary reaction product will exist in the resultant slurry as an impurity.

Hydroxyapatite powder is prepared from the slurry containing hydroxyapatite synthesized in such a manner. The present inventors have found that by using hydroxyapatite powder prepared from a slurry hardly containing the impurities mentioned above, it is possible for an obtained sintered compact to have high relative density, that is, it is possible to obtain a high-density sintered compact (a pellet for cell culture 1).

A description will now be made with regard to a preferred range of contents (concentrations) of each of tricalcium phosphate and unreacted substances ($Ca(OH)_2$, CaO) in the slurry.

(Tricalcium Phosphate)

The content (concentration) of tricalcium phosphate in the slurry is not limited to any specific value, but is preferably equal to or less than 0.1 wt %, and more preferably substantially close to 0 wt %. When the content of tricalcium phosphate in the slurry lies within such a range, it is possible for a resultant sintered compact to have higher density.

Further, it is most suitable that the slurry satisfies the condition A described below The condition A: A part of the slurry is sampled and then subjected to compression molding at a molding pressure of 2 ton/cm$^2$ to form a sample green compact having a detection surface. The sample green compact is sintered in an atmospheric air at 1,200° C. for 2 hours to obtain a sample sintered compact, and then substances which exist on the detection surface (having a surface roughness Ra of 10 μm) of the sample sintered compact are analyzed by x-ray diffraction. At this time, the intensity of a peak derived from hydroxyapatite is the largest among obtained peaks and a peak derived from tricalcium phosphate is not observed.

Such an analytical method is based on the fact that in the sintering process described above, grain growth of hydroxyapatite occurs prior to that of the impurities due to the difference in their sintering rates, and as a result the impurities are excluded from a void between the grains and then deposited on the surface of the sample sintered compact (in particular, on the detection surface). Therefore, by analyzing the detection surface by means of the X-ray diffraction, it is possible to detect the presence or absence of the impurities. According to this analytical method, it is possible to determine whether or not the impurities exist in the slurry with high accuracy.

When the slurry satisfies the condition A, it is confirmed that the slurry does not contain tricalcium phosphate or even if the slurry contains tricalcium phosphate, the amount thereof is extremely small. Therefore, by using such a slurry, it is possible to obtain especially high-density sintered compacts.

(Unreacted Substance)

The content (concentration) of the unreacted substance in the slurry is not limited to any specific value, but is preferably equal to or less than 3 wt %, and more preferably in the range of about 0.025 to 1 wt %. Even if a relatively small amount of the unreacted substance such as calcium oxide exists in the slurry, calcium oxide tends to increase the relative density of a resultant sintered compact (Note that, in a case where the unreacted substance is calcium hydroxide, calcium hydroxide is changed into calcium oxide due to sintering). As a result, an obtained sintered compact can have higher density. If the content of the unreacted substance in the slurry exceeds the above upper limit value, there is a case where it becomes difficult to obtain high-density sintered compacts depending on conditions during sintering of green compacts which will be described later.

Further, it is also most suitable that the slurry satisfies the condition B described below.

The condition B: A part of the slurry is sampled and then subjected to compression molding at a molding pressure of 2 ton/cm$^2$ to form a sample green compact having a detection surface. The sample green compact is sintered in an atmospheric air at 1,200° C. for 2 hours to obtain a sample sintered compact, and then substances which exist on the detection surface (having a surface roughness Ra of 10 μm) of the sample sintered compact are analyzed by X-ray diffraction. At this time, when the intensity of a peak derived from hydroxyapatite is defined as X and the intensity of a peak derived from calcium oxide is defined as Y, X and Y satisfy the relation Y/X<1/10 (especially, Y/X<1/100).

As described above, according to such an analytical method, it is also possible to determine whether or not the impurities exist in the slurry with high accuracy. When the slurry satisfies the condition B, it is confirmed that the content of the unreacted substance in the slurry is extremely small. By using such a slurry, it is also possible to obtain especially high-density sintered compacts.

Further, at least one of the contents of the tricalcium phosphate and the unreacted substance in the slurry should lie within the range described above, but it is preferred that both of the contents of the tricalcium phosphate and the unreacted substance lie within the respective ranges described above. This makes it possible to obtain extremely high-density sintered compacts.

Next, hydroxyapatite powder (hereinafter, simply referred to as "powder") is prepared by, for example, spray drying the thus obtained slurry.

The mean particle size of the powder is not limited to any specific value, but is preferably in the range of about 1 to 30 μm, and more preferably in the range of about 8 to 25 μm. By using powder having such a mean particle size, it is possible to obtain higher-density sintered compacts.

It is to be noted here that the obtained powder may be subjected to heat treatment under the condition of 500 to 800° C. for 2 to 6 hours, for example, and then milled using, for example, a jet mill or a turbo mill so that the powder has a mean particle size of about 6 to 20 μm (which is about 50 to 90% of a mean particle size before milling). By using such milled powder, it is possible to obtain more closely compacted green compacts.

<2C> Molding of Green Compact

Next, the thus obtained powder (or a powder compact which has been molded into a desired form in advance) is compacted by the application of pressure.

As for a method of applying pressure, any method such as isotropic pressing, pressing in only one direction (uniaxial direction) e.g., uniaxial pressing, or the like can be employed. Among them, isotropic pressing, especially hydrostatic pressing is preferable. By using such a method, it is possible for a resultant green compact to have uniform density, and as a result, a higher-density sintered compact can be obtained.

As for hydrostatic pressing, CIP (Cold Isostatic pressing) in which pressure is applied at a temperature of about 5 to 50° C. (preferably, about 10 to 30° C.) is suitably used. Since CIP has such advantages that it can be carried out with simple equipment and that a film (which will be described later) is not required to have heat resistance, CIP is practically useful as a technique for use in manufacturing industrial products. Alternatively, HIP (Hot Isostatic pressing) in which pressure is applied with heating (at 65° C. or higher, for example), or Hot press may be employed.

Specifically, in hydrostatic pressing, the powder enclosed with a liquid-proof film is placed in a hydrostatic pressing unit, and then hydrostatic pressure is applied. In the case of CIP, examples of a material of the film include: resin such as polyvinyl chloride, polyethylene, polypropylene and the like; and rubber such as natural rubber and isoprene rubber. The film can be formed by, for example, dipping or vacuum packing.

A pressure to be applied is 1 ton/cm$^2$ or higher, more preferably in the range of about 1 to 3 ton/cm$^2$, and even more preferably in the range of about 2 to 3 ton/cm$^2$. If the pressure is too low, there is a case where a sufficient effect by pressing (especially, uniformity in density) can not be expected. On the other hand, even if the pressure is increased so as to exceed the above upper limit value, an improved effect can not be obtained. Further, use of such an increased pressure requires large-scale equipment, thus resulting in an increased equipment cost.

The green compact obtained by applying pressure in this manner can have high and uniform density. When such a green compact is sintered as described below, the green compact is uniformly shrunk. Therefore, an obtained sintered compact has high dimensional accuracy. Further, such uniform density suppresses the occurrence of sintering flaws such as cracking, chipping, and the like in the sintered compact, and therefore such a sintered compact is hard to be damaged (that is, it has excellent mechanical strength). In this connection, the film covering the surface of the powder is removed by a predetermined method after pressing.

<3C> Shaping of Green Compact

Next, the thus obtained green compact is shaped into a desired form or size, as necessary.

The green compact is shaped by, for example, subjecting it to a predetermined machine working. Examples of such machine working include cutting, grinding, polishing and the like, and they can be carried out singly or in combination of two or more.

Since the hardness of the green compact itself is very low as compared with that of an obtained sintered compact, it is possible to easily carry out the machine working or the like onto the green compact. In particular, the green compact has advantages in that the machine working can be carried out with low hardness tools and it takes shorter time to complete the machine working.

<4C> Sintering of Green Compact

The thus obtained green compact is sintered (fired) in an oxygen-containing atmosphere in a sintering furnace, for example, in which the partial pressure of oxygen is higher than that in an atmospheric air, thereby to obtain a sintered compact.

The present inventors have conducted extensive research, and as a result found that by sintering the green compact in an oxygen-containing atmosphere in which the partial pressure of oxygen is higher than that in an atmospheric air, it is possible to obtain especially high-density sintered compacts.

A typical example of such an oxygen-containing atmosphere (sintering atmosphere) includes a pure oxygen atmosphere. Alternatively, a mixed gas of oxygen and other gases (in particular, a mixed gas mainly containing oxygen) may be used as the oxygen-containing atmosphere.

Further, in a case where the green compact is sintered under pressure higher than atmospheric pressure (2 to 10 atoms, for example), an atmospheric air may be used as the oxygen-containing atmosphere, because a resultant partial pressure of oxygen therein becomes higher than that in an atmospheric air. Alternatively, it is possible to sinter green compacts in a sealed furnace containing only a small amount of oxygen at atmospheric pressure or lower. In this case, since there is no necessity to continue supplying oxygen gas, the amount of oxygen to be used can be reduced.

It is to be noted here that in a case where the green compact is sintered under atmospheric pressure (1 atom), it is not necessary for a sintering furnace to have high airtightness. Therefore, sintering under atmospheric pressure is preferred in that a sintering furnace can be simplified, thus resulting in a reduced manufacturing cost of pellets for cell culture.

The partial pressure of oxygen in the oxygen-containing atmosphere (in the case of a pure oxygen atmosphere, the partial pressure of oxygen means a pressure in the sintering furnace) is preferably equal to or higher than 380 mmHg, and more preferably equal to or higher than 550 mmHg. By setting the partial pressure of oxygen to the above range, it is possible for an obtained sintered compact to have higher relative density.

In this connection, under atmospheric pressure, by increasing the volume (concentration) of oxygen in the oxygen-containing atmosphere (sintering atmosphere), the partial pressure of oxygen in the oxygen-containing atmosphere becomes high.

Further, the present inventors have found that by sintering the green compact in such an oxygen-containing atmosphere in which the partial pressure of oxygen is high, it is possible to carry out sintering at a relatively low sintering temperature. Further, they have also found that in this case the green compact can be sintered while the grain growth of hydroxyapatite is being suppressed and as a result higher-density sintered compacts can be obtained.

Furthermore, sintering of green compacts at a relatively low temperature also has advantages in that sintering time, energy consumed for sintering and the cost of a heating element used in a sintering furnace can be reduced.

A temperature during sintering (sintering temperature) is in the range of 925 to 1,300° C., and is preferably in the range of about 1,000 to 1,250° C. If the sintering temperature is too low, there is a case that the green compact is not efficiently sintered so that a resultant sintered compact is slightly warped.

A period of time over which the sintering temperature is being held (sintering time) is preferably in the range of about 30 minutes to 8 hours, and is more preferably in the range of about 2 to 4 hours.

After the completion of the sintering, the obtained sintered compact may further be sintered in an atmosphere with low level of activity.

<5C> Grinding or Polishing of Sintered Compacts

Next, each of the surfaces of the thus obtained sintered compact is ground and/or polished with an abrasive (that is, the grinding material and the polishing material as described above) which is appropriately selected according to its target surface property, to thereby form a cell adhesion surface 2 and an observation surface 3.

Through the steps described above, a pellet for cell culture 1 shown in FIG. 3 can be obtained.

Since the density of such a pellet for cell culture 1 is high, the transparency and mechanical strength thereof are also extremely high.

In this regard, it is to be noted that the method for manufacturing such a pellet for cell culture 1 may include a preliminary step coming before the step 1C, an intermediate step coming between the step 1C and the step 5C, or a post step coming after the step 5C depending on particular objectives.

Further, the step of grinding and/or polishing (step 5C) may be omitted. In this case, an obtained sintered compact can be used as it is as a pellet for cell culture 1, in which the cell adhesion surface 2 and the observation surface 3 both provide smooth surfaces.

Furthermore, in the step 5C, both of the cell adhesion surface 2 and the observation surface 3 may be subjected to grinding to provide rough surfaces or may be subjected to mirror polishing to provide specular surfaces.

SECOND EMBODIMENT

Figure 6:
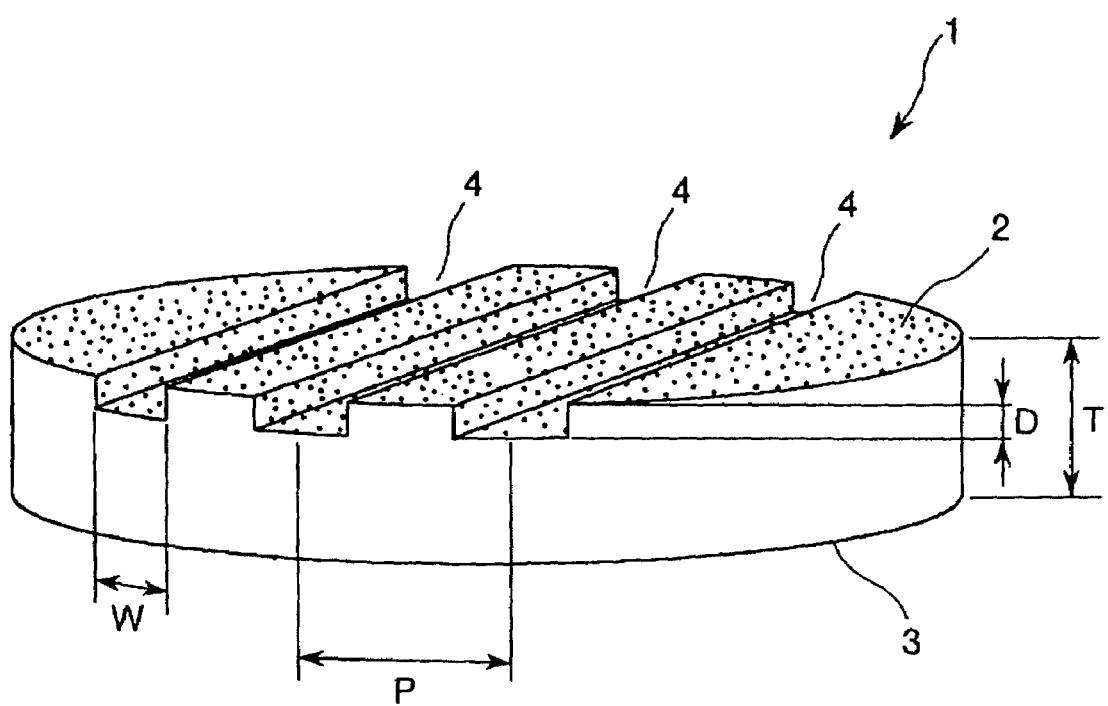
FIG. 6 is a perspective view which shows a second embodiment of the cell culture base of the present invention, in which the present invention is applied to a pellet for cell culture.

FIG. 6 is a perspective view which shows a second embodiment of the cell culture base of the present invention, in which the present invention is applied to a pellet for cell culture. In this connection, in the following description, the upper side and the lower side in FIG. 6 will be referred to as "top" and "bottom", respectively.

Hereinbelow, a pellet for cell culture 1 of the second embodiment will be explained by focusing the difference between the first and second embodiments, and explanation with regard to the overlapping points is omitted.

The pellet for cell culture 1 shown in FIG. 6 is the same as the pellet for cell culture 1 of the first embodiment except that a concave part comprised of a plurality of straight grooves 4 provided substantially parallel with one another is formed in the cell adhesion surface 2.

By providing such a concave part in the cell adhesion surface 2, it is possible to increase (control) the surface area of the cell adhesion surface 2. That is, an area (region) where cells can adhere can be increased. This further facilitates quick adhesion of cells to the pellet for cell culture 1 so that more efficient cell culture becomes possible.

Further, the concave part serves as a marker indicating that a surface having such a concave part is the cell adhesion surface 2. This helps users in using the pellet for cell culture 1.

As shown in the present embodiment, when the grooves 4 are provided as the concave part, cells grow (in line) along edges of the grooves 4. Therefore, it is possible to easily observe the cells (in particular, the degree of cell growth or the like). In this connection, the grooves 4 can be formed relatively easily.

As shown in FIG. 6, the horizontal cross-sectional area of each groove 4 (the width of each groove 4) is substantially constant in the direction of depth so that the cross section of the groove 4 is in the shape of a letter C. This makes it easy for cells to adhere to the edges of the grooves 4.

The percentage of an area occupied by the grooves 4 to the whole surface area of the pellet for cell culture 1 in a plan view is preferably in the range of about 1 to 60%, and more preferably in the range of about 10 to 30%. By setting the percentage of an area occupied by the grooves 4 to the whole area of the pellet for cell culture 1 in a plan view to the above range, it is possible to sufficiently increase the surface area of the cell adhesion surface 2.

In a case where the diameter of the pellet for cell culture 1 is set to the same range as that of the first embodiment, the width of the groove 4 (that is a dimension W in FIG. 6) is preferably set to the range of about 0.001 to 2 mm, and more preferably set to the range of about 0.01 to 1 mm. Further, a space between adjacent grooves 4 (that is a dimension P in FIG. 6) is preferably set to the range of about 0.001 to 5 mm, and more preferably set to the range of about 0.01 to 2 mm.

Further, the percentage of the depth of the groove (concave part) 4 (that is a dimension D in FIG. 6) to the thickness of the pellet for cell culture 1 (that is a dimension T in FIG. 6) is preferably in the range of about 0.005 to 20%, and more preferably in the range of about 0.01 to 10%. By setting the percentage of the depth of the groove 4 to the thickness of the pellet for cell culture 1 to the above range, it is possible to sufficiently increase the surface area of the cell adhesion surface 2, while the pellet for cell culture 1 possesses sufficient strength.

Such grooves 4 can be formed by subjecting a green compact to machine working in the step 3C in the manufacturing process of the pellet for cell culture 1 described in the first embodiment.

Also in a case where such a pellet for cell culture 1 of the second embodiment described above is used, it is possible to obtain the same effects as in the case where the pellet for cell culture 1 of the first embodiment is used.

THIRD EMBODIMENT

Figure 7:
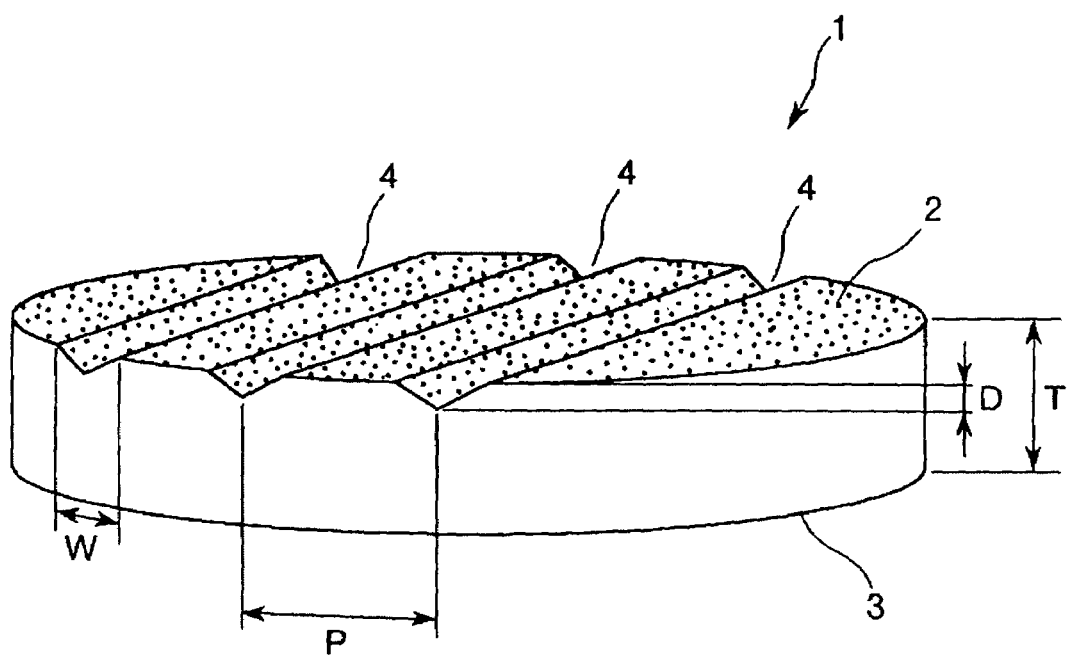
FIG. 7 is a perspective view which shows a third embodiment of the cell culture base of the present invention, in which the present invention is applied to a pellet for cell culture.

FIG. 7 is a perspective view which shows a third embodiment of the cell culture base of the present invention, in which the present invention is applied to a pellet for cell culture. In this connection, in the following description, the upper side and the lower side in FIG. 7 will be referred to as "top" and "bottom", respectively.

Hereinbelow, a pellet for cell culture 1 of a third embodiment will be explained by focusing the difference between the first and second embodiments and third embodiment, and explanation with regard to the overlapping points is omitted.

The pellet for cell culture shown in FIG. 7 is the same as the pellet for cell culture 1 of the second embodiment described above except that the shape of each groove 4 is different from that of the groove of the second embodiment.

As shown in FIG. 7, the horizontal cross-sectional area of the groove 4 (the width of the groove 4) is decreased toward the observation surface (another surface) 3 so that the cross-section of the groove 4 is in the shape of a letter V.

In this case, the maximum width of the groove 4 is set so as to lie within the same range as the width of the groove 4 of the second embodiment.

Such grooves 4 can be formed by subjecting a green compact to machine working in the step 3C in the manufacturing process of the pellet for cell culture 1 described in the first embodiment.

Also in a case where such a pellet for cell culture 1 of the third embodiment described above is used, it is possible to obtain the same effects as in the case where the pellet for cell culture 1 of the first embodiment or second embodiment is used.

It is to be noted here that the groove 4 is not necessarily limited to a groove having a straight shape as described in the second and third embodiments. For example, the groove 4 may have a meandering shape, a spiral shape or the like. Alternatively, the grooves 4 may be arranged so as to form a grid pattern, for example.

Further, the cross section of the groove 4 may have a substantially U-shape, instead of a substantially C-shape (the second embodiment) or a substantially V-shape (the third embodiment).

Furthermore, although a description has been made with regard to the pellet for cell culture 1 having the disk-like shape (a circular shape in a plan view) as an example in each of the embodiments, the shape of the pellet for cell culture 1 in a plan view is not limited to any specific one, and the pellet may be formed so as to have various shapes such as triangle, quadrangle (square, rectangle, rhombus), hexagon, ellipse or the like, for example.

Moreover, it should be noted that although a description has been made with regard to the cell culture base and the method for manufacturing cell culture bases according to the present invention, the present invention is not limited thereto.

The cell culture base of the present invention has a flat plate portion which enables cells to adhere thereto and grow in at least one of surfaces thereof. In each of the embodiments described above, a description has been made with regard to the pellets for cell culture as the representative of the cell culture base of the present invention, in which the cell culture base itself is composed from the flat plate portion which enables cells to adhere thereto and grow, that is the flat plate portion constitutes the entire of the cell culture base. However, the cell culture base of the present invention may be provided with a portion (that is the part which enables cells to adhere and grow) which has a structure described in any one of the embodiments as a bottom part of the cell culture base.

Examples of such a cell culture base include a petri dish, an Erlenmeyer flask, a microplate, a tube and the like. In these examples, the bottom parts thereof may be formed from any one of the cell culture bases shown in these embodiments.

Further, a method for observing the condition of cells is not limited to a method in which light is allowed to pass through the part which enables cells to adhere and grow. It goes without saying that a method using an electron microscope may be employed, for example.

Example

Next, a description will be made with regard to actual examples of the cell culture base according to the present invention.

<Manufacture of Pellet for Cell Culture (Cell Culture Base)>

20 pellets for cell culture were made in each of Examples 1C to 6C and Comparative Examples 1C and 2C as follows.

Example 1C

<1> First, 140 g of calcium hydroxide was dispersed in 6 liters of pure water, and then an aqueous phosphoric acid solution whose concentration of phosphoric acid was 2 wt % was dropped into the pure water in which calcium hydroxide was dispersed. They were sufficiently mixed with stirring to synthesize hydroxyapatite, and as a result a slurry containing hydroxyapatite was obtained.

Next, the thus obtained slurry was spray dried using a spray dryer to obtain hydroxyapatite powder having a mean particle size of 20 μm.

Here, a part of the slurry was sampled and then subjected to compression molding at a molding pressure of 2 ton/cm$^2$ to form a sample green compact having a detection surface. The thus obtained sample green compact was sintered in an atmospheric air at 1,200° C. for 2 hours to obtain a sample sintered compact, and then substances existing on the detection surface (having a surface roughness Ra of 10 μm) of the sample sintered compact were analyzed by X-ray diffraction. In this connection, the sample had a diameter of 15 mm and a height of 8 mm.

As a result of analysis, a peak derived from tricalcium phosphate (TCP) was not observed, and the intensity of a peak derived from calcium oxide (CaO) was 1/250 of that derived from hydroxyapatite (HAp).

The thus obtained hydroxyapatite powder was subjected to heat treatment under the condition of 600° C. for 4 hours, and was then milled using a jet mill. In this way, hydroxyapatite powder having a mean particle size of 16 μm was obtained.

<2> Next, the thus obtained hydroxyapatite powder was compressed into a disk-like shape by the use of a compression molding machine, and thereafter the powder formed into the disk-like shape was put into a plastic bag and vacuum-sealed. Then, compression molding was carried out under the condition of a hydrostatic pressure of 2 ton/cm$^2$ at room temperature (24° C.), to thereby obtain a disk-shaped green compact.

<3> Next, machine working was carried out on the green compact by the use of a lathe so that the green compact had a diameter of 28 mm and a thickness of 1.4 mm.

<4> Next, the thus obtained green compact was sintered in a sintering furnace to obtain a sintered compact having a diameter of 20 mm and a thickness of 1 mm. In this regard, it is to be noted that sintering was carried out in a pure oxygen atmosphere (sintering atmosphere) at 1,050° C. for 2 hours. At this time, a pressure in the sintering furnace was set to 760 mmHg (1 atom).

The obtained sintered compact had a porosity of 0.5%. The porosity of the sintered compact was measured by Archimedes method. This sintered compact was used as a pellet for cell culture.

Further, light transmittance at the time when light of wavelength of 600 nm was allowed to pass through the pellet for cell culture in the thickness direction thereof was 3%.

Example 2C

A pellet for cell culture was manufactured in the same manner as Example 1C except that the sintering temperature was changed to 1,200° C. in the process <4> described above. In this connection, the porosity of the pellet for cell culture was 0.4%.

Further, light transmittance at the time when light of wavelength of 600 nm was allowed to pass through the pellet for cell culture in the thickness direction thereof was 4%.

Example 3C

A pellet for cell culture was manufactured in the same manner as Example 1C except that one of the surfaces (cell adhesion surface) of the pellet was ground with an abrasive (grinding material) containing diamond particles having a mean particle size of 25 μm, and another surface (observation surface) was polished with an abrasive (polishing material) containing diamond particles having a mean particle size of 0.5 μm after the process <4> described above. In this connection, the porosity of the pellet for cell culture was 0.5%.

Further, light transmittance at the time when light of wavelength of 600 nm was allowed to pass through the pellet for cell culture in the thickness direction thereof was 3%.

Example 4C

A pellet for cell culture was manufactured in the same manner as Example 1C except that both of the surfaces of the pellet for cell culture were polished with an abrasive (polishing material) containing diamond particles having a mean particle size of 0.5 μm after the process <4> described above. In this connection, the porosity of the pellet for cell culture was 0.5%.

Further, light transmittance at the time when light of wavelength of 600 nm was allowed to pass through the pellet for cell culture in the thickness direction thereof was 6%.

Example 5C

A pellet for cell culture was manufactured in the same manner as Example 1C except that cutting was carried out onto the green compact so that grooves each having a C-shaped cross section were formed in one of the surfaces (cell adhesion surface) of the pellet for cell culture in the process <3> described above. In this connection, the porosity of the pellet for cell culture was 0.5%.

Further, light transmittance at the time when light of wavelength of 600 nm was allowed to pass through the pellet for cell culture in the thickness direction thereof was 3%.

Furthermore, the width of the groove was 0.1 mm, a space between the adjacent grooves was 0.5 mm, the percentage of an area occupied by the grooves to the whole area of the pellet for cell culture in a plan view was 20%, and the percentage of the depth of the groove to the thickness of the pellet for cell culture was 6.5%.

Example 6C

A pellet for cell culture was manufactured in the same manner as Example 5C except that the cross section of the groove was in the shape of a letter V. In this connection, the porosity of the pellet for cell culture was 0.5%.

Further, light transmittance at the time when light of wavelength of 600 nm was allowed to pass through the pellet for cell culture in the thickness direction was 3%.

Furthermore, the width of the groove was 0.1 mm, a space between the adjacent grooves was 0.5 mm, the percentage of an area occupied by the grooves to the whole area of the pellet for cell culture in a plan view was 20%, and the percentage of the depth of the groove to the thickness of the pellet for cell culture was 6.5%.

Comparative Example 1C

A pellet for cell culture was manufactured in the same manner as Example 1 excepting the following processes.

First, hydroxyapatite powder was prepared in the same manner as Example 1C. The obtained hydroxyapatite powder was mixed with an aqueous methylcellulose solution, to thereby obtain a slurry. Then, the slurry was stirred so that the slurry contained air bubbles. Next, the thus obtained slurry was supplied into a mold and then dried to obtain a green compact.

Next, the green compact was sintered in an atmospheric air at 1,050° C. for 2 hours to obtain a porous sintered compact.

The porosity of the obtained sintered compact was 50%. This sintered compact was used as a pellet for cell culture.

Comparative Example 2C

A pellet for cell culture made of polystyrene and having a disk-like shape (having a diameter of 20 mm and a thickness of 1 mm) was manufactured.

Evaluation

Human osteosarcoma cells (HOS) were cultured using the pellets for cell culture manufactured in each of Examples 1C to 6C and Comparative Examples 1C and 2C, and then evaluations were made as follows.

First, primary culture of human osteosarcoma cells was prepared in a flask, and the primary cultured human osteosarcoma cells were then trypsinized. The human osteosarcoma cells were suspended in a culture medium to obtain a cell suspension containing $1 \times 10^5$ human osteosarcoma cells/ml.

In this regard, it is to be noted that the culture medium used was MEM containing 10 vol % of FBS and 1 vol % of NEAA.

Next, 20 pellets for cell culture manufactured in each of Examples 1C to 6C and Comparative Examples 1C and 2C were individually put into a well of the plate as shown in FIG. 4, and then 2 ml of the cell suspension was supplied into each well.

In such a state, human osteosarcoma cells were cultured at 37° C. under the current of mixed gas of 95 vol % of $O_2$ and 5 vol % of $CO_2$.

After one hour has elapsed from the supply of the cell suspension, 10 pellets for cell culture of each of Examples 1C to 6C and Comparative Examples 1C and 2C were taken out of the wells, and then trypan blue staining was performed on the human osteosarcoma cells.

Then, in a state that the pellet for cell culture was being irradiated with light from the side of one surface (cell adhesion surface), the condition of the human osteosarcoma cells was observed from the side of another surface (observation surface) by the use of an optical microscope ("research inverted system microscope IX71" made by OLYMPUS OPTICAL CO., LTD.), and the number of the human osteosarcoma cells existing on the cell adhesion surface of each pellet for cell culture was counted.

Further, after two days have elapsed from the supply of the cell suspension, the remaining 10 pellets for cell culture of each of Examples 1C to 6C and Comparative Examples 1C and 2C were taken out of the wells, and then the same operations as those described above were carried out.

As a result, in each of the cases of Examples 1C to 6C and Comparative Example 2C, it was possible to observe the condition of human osteosarcoma cells (that is, it was possible to count the number of human osteosarcoma cells). On the other hand, in the case of Comparative Example 1C, since light was not allowed to pass through the pellet for cell culture, it was difficult to observe the condition of human osteosarcoma cells.

Further, it has been confirmed that the number of human osteosarcoma cells adhered to the cell adhesion surfaces of the pellets for cell culture of each of Examples 1C to 6C was equal to or larger than that of each of Comparative Examples 1C and 2C. Further, it has been also confirmed that the number of human osteosarcoma cells adhered to the pellets for cell culture of Example 3C each having the rough surface as the cell adhesion surface, the number of human osteosarcoma cells adhered to the pellets for cell culture of Example 5C each provided with the grooves in the cell adhesion surface thereof, and the number of human osteosarcoma cells adhered to the pellets for cell culture of Example 6C each provided with the grooves in the cell adhesion surface thereof were especially large.

Further, after two days have elapsed from the supply of the cell suspension, a significant growth of human osteosarcoma cells was confirmed on the pellets for cell culture of each of Examples 1C to 6C and Comparative Examples 1C and 2C.

Furthermore, the cells adhered to the pellets for cell culture of each of Examples 1C to 6C were not come off even when the culture medium was replaced so that it has been confirmed that the cells firmly adhered to the pellets for cell culture. In particular, in the cases of the pellets for cell culture of Example 3C each having the rough surface as the cell adhesion surface, the pellets for cell culture of Example 5C each provided with the grooves in the cell adhesion surface thereof, and the pellets for cell culture of Example 6C each provided with the grooves in the cell adhesion surface thereof, the cells adhered to the pellets for cell culture were not come off even in a case where the pellets for cell culture were roughly handled, so that it has been confirmed that that cells more firmly adhered.

Figure 8:
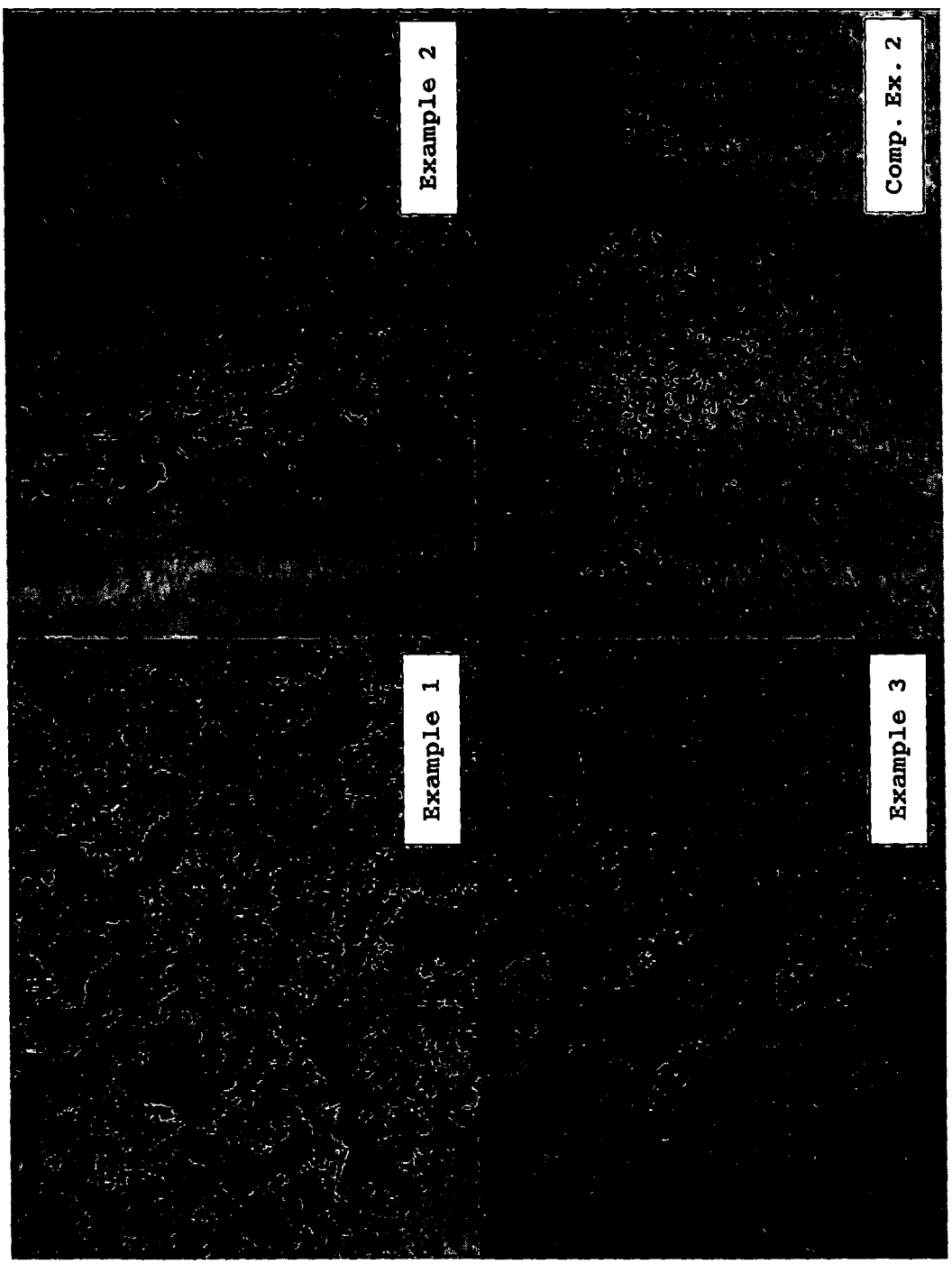
FIG. 8 is an optical microscope photograph which shows observation images of the pellets for cell culture of Examples 1 to 3 and Comparative Example 2 observed after a lapse of two days from the beginning of cell culture.

In this connection, observation images (visual image) of the pellets for cell culture of Examples 1C to 3C and Comparative Example 2C by an optical microscope at the time when two days have elapsed were shown in FIG. 8 as examples.

Further, it was possible to observe the pellets for cell culture of each of Examples 1C to 6C by the use of the optical microscope even in a case where staining was not performed on human osteosarcoma cells as was the case with the pellets for cell culture of Comparative Example 2C.

As has been described above, according to the cell culture base of the present invention, it is possible to allow cells to efficiently adhere and grow. Further, since a flat plate portion which enables cells to adhere and grow has high transparency, it is possible to observe the condition of the cells by a simple method in which light is allowed to pass through the flat plate portion on which the cells are adhered to grow.

In particular, since the flat plate portion which enables cells to adhere and grow is mainly composed of a calcium phosphate based compound, it is possible to culture cells in conditions similar to those in a living body and to properly evaluate the affinity of various cells with bone.

Further, by appropriately setting the surface property of the flat plate portion which enables cells to adhere and grow, the effects described above can be further improved.

Furthermore, in a case where the entire of the cell culture base of the present invention constitutes the flat plate portion which enables cells to adhere and grow, by appropriately setting the dimensions of such a cell culture base, it is also possible to transplant the cell culture base itself with cultured cells into a living body.

Finally, it is to be understood that many changes and additions may be made to the embodiments described above without departing from the scope and spirit of the present invention as defined in the following claims.

Further, it is also to be understood that the present disclosure relates to subject matters contained in Japanese Patent Applications No. 2002-235210 (filed on Aug. 12, 2002), No. 2003-271182 (filed on Jul. 4, 2003) and No. 2002-339822 (filed on Nov. 22, 2002) which are expressly incorporated herein by reference in their entireties.

What is claimed is:

1. A method for manufacturing a sintered compact, comprising:
   molding a green compact by compacting hydroxyapatite powder with applying a pressure of 1 ton/cm$^2$ or higher thereto; and
   sintering the green compact in an oxygen-containing atmosphere, in which the partial pressure of oxygen in the oxygen-containing atmosphere is 380 mmHg or higher, at a temperature in the range of 925 to 1,300° C. to obtain a sintered compact.

2. The method as claimed in claim 1, wherein the pressure is isotropically applied to the hydroxyapatite powder.

3. The method as claimed in claim 2, wherein the isotropic pressure is applied by hydrostatic pressing.

4. The method as claimed in claim 3, wherein the hydrostatic pressing is carried out at a temperature in the range of 5 to 50° C.

5. The method as claimed in claim 1, wherein the hydroxyapatite powder is prepared from a slurry which is obtained by reacting a calcium source with a phosphoric acid source and wherein at least one of the calcium source and the phosphoric acid source is used in a liquid form.

6. The method as claimed in claim 5, wherein the calcium source contains calcium hydroxide or calcium oxide as a main ingredient, and the phosphoric acid source contains phosphoric acid as a main ingredient.

7. The method as claimed in claim 6, wherein the slurry contains as a secondary reaction product tricalcium phosphate of 0.1 wt % or less.

8. The method as claimed in claim 6, wherein after reacting the calcium source and phosphoric acid source to obtain hydroxyapatite unreacted calcium hydroxide or calcium oxide contained in the slurry is in the range of 0 to 3 wt %.

* * * * *